United States Patent
Sharkawy et al.

(10) Patent No.: US 8,512,360 B2
(45) Date of Patent: Aug. 20, 2013

(54) CONDUITS FOR USE IN PLACING A TARGET VESSEL IN FLUID COMMUNICATION WITH SOURCE OF BLOOD

(75) Inventors: A. Adam Sharkawy, Union City, CA (US); Dean F. Carson, Mountain View, CA (US); Darin C. Gittings, Sunnyvale, CA (US); Keke J. Lepulu, Redwood City, CA (US); Mark J. Foley, Menlo Park, CA (US); Wally S. Buch, Atherton, CA (US); Alan R. Rapacki, Redwood City, CA (US)

(73) Assignee: Medtronic, Inc., Minneapolis, MN (US)

( * ) Notice: Subject to any disclaimer, the term of this patent is extended or adjusted under 35 U.S.C. 154(b) by 3184 days.

(21) Appl. No.: 10/778,723

(22) Filed: Feb. 13, 2004

(65) Prior Publication Data

US 2004/0168691 A1    Sep. 2, 2004

Related U.S. Application Data

(63) Continuation of application No. 09/393,131, filed on Sep. 10, 1999, now abandoned, which is a continuation-in-part of application No. 09/023,492, filed on Feb. 13, 1998, now abandoned, which is a continuation-in-part of application No. 09/232,103, filed on Jan. 15, 1999, now abandoned, which is a continuation-in-part of application No. 09/232,062, filed on Jan. 15, 1999, now abandoned.

(51) Int. Cl.
*A61B 17/08* (2006.01)
*A61M 5/00* (2006.01)

(52) U.S. Cl.
USPC .......................................... 606/153; 604/284

(58) Field of Classification Search
USPC ........ 606/153, 108; 604/284, 264; 623/1.36, 623/1.15, 1.13; 128/898
See application file for complete search history.

(56) References Cited

U.S. PATENT DOCUMENTS

| 2,127,903 A | 8/1938 | Bowen |
| 2,453,056 A | 11/1948 | Zack |

(Continued)

FOREIGN PATENT DOCUMENTS

| EP | 0121795 A2 | 10/1984 |
| EP | 0479478 | 4/1992 |

(Continued)

OTHER PUBLICATIONS

Acuff, et al., Minimally Invasive Coronary Artery Bypass Grafting, Ann. Thorac. Surg., 1996,.61:135-137.

(Continued)

*Primary Examiner* — Julian Woo

(57) ABSTRACT

Methods and devices for placing a target vessel in fluid communication with a source of blood and a target vessel. A conduit includes first portion adapted to be placed in fluid communication with a source of blood, such as a heart chamber, and a second portion adapted to be placed in fluid communication with a target vessel having a lumen, such as coronary artery. The first and second conduit portions are transverse to each other such that the conduit is generally T-shaped. The conduit lies on an exterior of the heart between the blood source and the target vessel and is configured to deliver blood in multiple directions into the lumen of the target vessel. For example, in an occluded coronary artery, blood flows both toward and away from the occlusion. The conduit may be flexible, rigid, collapsible or non-collapsible, and may be formed of synthetic vascular graft material, tissue, or a combination of the two. A conduit delivery device is disclosed for deploying the conduit in a target vessel and perfusing the vessel during such deployment.

4 Claims, 23 Drawing Sheets

(56) References Cited

U.S. PATENT DOCUMENTS

| | | |
|---|---|---|
| 3,042,021 A | 7/1962 | Read |
| 3,316,914 A | 5/1967 | Collito |
| 3,540,451 A | 11/1970 | Zeman |
| 3,774,615 A | 11/1973 | Lim et al. |
| 3,901,965 A | 8/1975 | Honeyman, III |
| 3,970,401 A | 7/1976 | Lubeck |
| 3,995,617 A | 12/1976 | Watkins et al. |
| 4,011,872 A | 3/1977 | Komiya |
| 4,072,153 A * | 2/1978 | Swartz ............ 604/284 |
| 4,142,528 A * | 3/1979 | Whelan et al. ........ 604/284 |
| 4,284,459 A | 8/1981 | Patel et al. |
| 4,300,244 A | 11/1981 | Bokros |
| 4,368,736 A | 1/1983 | Kaster |
| 4,400,833 A | 8/1983 | Kurland |
| 4,523,592 A | 6/1985 | Daniel |
| 4,546,499 A | 10/1985 | Possis et al. |
| 4,562,597 A | 1/1986 | Possis et al. |
| 4,581,017 A | 4/1986 | Sahota et al. |
| 4,712,551 A | 12/1987 | Rayhanabad |
| 4,728,328 A | 3/1988 | Hughes et al. |
| 4,769,029 A | 9/1988 | Patel |
| 4,769,031 A | 9/1988 | McGough et al. |
| 4,822,341 A | 4/1989 | Colone |
| 4,861,330 A | 8/1989 | Vos |
| 4,862,886 A | 9/1989 | Clark et al. |
| 4,873,043 A | 10/1989 | Meyers |
| 4,902,289 A | 2/1990 | Yannes |
| 4,953,553 A | 9/1990 | Tremulis |
| 4,955,856 A | 9/1990 | Phillips |
| 4,955,899 A | 9/1990 | Della Corna et al. |
| 4,976,691 A | 12/1990 | Sahota |
| 4,985,014 A | 1/1991 | Orejola |
| 4,995,857 A | 2/1991 | Arnold |
| 5,054,484 A | 10/1991 | Hebeler, Jr. |
| 5,071,406 A | 12/1991 | Jang |
| 5,078,735 A | 1/1992 | Mobin-Uddin |
| 5,100,423 A | 3/1992 | Fearnot |
| 5,106,386 A | 4/1992 | Isner et al. |
| 5,111,832 A | 5/1992 | Saksena |
| 5,131,406 A | 7/1992 | Kaltenbach |
| 5,143,093 A | 9/1992 | Sahota |
| 5,184,610 A * | 2/1993 | Marten et al. ........ 604/284 |
| 5,190,058 A | 3/1993 | Jones et al. |
| 5,209,731 A | 5/1993 | Sterman et al. |
| 5,211,624 A | 5/1993 | Cinberg et al. |
| 5,250,058 A | 10/1993 | Miller et al. |
| 5,254,097 A | 10/1993 | Schock et al. |
| 5,254,113 A | 10/1993 | Wilk |
| 5,256,150 A | 10/1993 | Quiachon et al. |
| 5,275,622 A | 1/1994 | Lazarus et al. |
| 5,287,861 A | 2/1994 | Wilk |
| 5,302,336 A | 4/1994 | Hartel et al. |
| 5,314,436 A | 5/1994 | Wilk |
| 5,318,527 A | 6/1994 | Hyde et al. |
| 5,327,193 A | 7/1994 | Date et al. |
| 5,327,913 A | 7/1994 | Taheri |
| 5,330,500 A | 7/1994 | Song |
| 5,336,176 A | 8/1994 | Yoon |
| 5,356,587 A | 10/1994 | Mitsui et al. |
| 5,370,685 A | 12/1994 | Stevens |
| 5,380,316 A | 1/1995 | Aita et al. |
| 5,383,892 A | 1/1995 | Cardon et al. |
| 5,383,925 A | 1/1995 | Schmitt |
| 5,389,096 A | 2/1995 | Aita et al. |
| 5,395,349 A | 3/1995 | Quiachon et al. |
| 5,397,320 A | 3/1995 | Essig et al. |
| 5,409,019 A | 4/1995 | Wilk |
| 5,425,705 A | 6/1995 | Evard et al. |
| 5,425,765 A | 6/1995 | Tiefenbrun et al. |
| 5,429,144 A | 7/1995 | Wilk |
| 5,440,551 A | 8/1995 | Suzuki |
| 5,443,497 A | 8/1995 | Venbrux |
| 5,452,733 A | 9/1995 | Sterman et al. |
| 5,456,714 A | 10/1995 | Owen |
| 5,458,574 A | 10/1995 | Machold et al. |
| 5,466,242 A | 11/1995 | Mori |
| 5,478,309 A | 12/1995 | Sweezer et al. |
| 5,484,418 A | 1/1996 | Quiachon et al. |
| 5,488,958 A | 2/1996 | Topel et al. |
| 5,489,295 A | 2/1996 | Piplani et al. |
| 5,494,041 A | 2/1996 | Wilk |
| 5,501,698 A | 3/1996 | Roth et al. |
| 5,503,635 A | 4/1996 | Sauer et al. |
| 5,505,725 A | 4/1996 | Samson |
| 5,522,880 A | 6/1996 | Barone et al. |
| 5,549,581 A | 8/1996 | Lurie et al. |
| 5,591,226 A | 1/1997 | Trerotola et al. |
| 5,603,722 A | 2/1997 | Phan et al. |
| 5,613,069 A | 3/1997 | Walker |
| 5,620,439 A | 4/1997 | Abela et al. |
| 5,643,340 A | 7/1997 | Nunokawa |
| 5,649,952 A | 7/1997 | Lam |
| 5,653,743 A | 8/1997 | Martin |
| 5,655,548 A | 8/1997 | Nelson et al. |
| 5,662,124 A | 9/1997 | Wilk |
| 5,665,114 A | 9/1997 | Weadock et al. |
| 5,676,670 A | 10/1997 | Kim |
| 5,683,640 A | 11/1997 | Miller et al. |
| 5,689,550 A | 11/1997 | Garson et al. |
| 5,690,656 A | 11/1997 | Cope et al. |
| 5,695,504 A | 12/1997 | Gifford, III et al. |
| 5,697,943 A | 12/1997 | Sauer et al. |
| 5,702,412 A | 12/1997 | Popov et al. |
| 5,713,950 A | 2/1998 | Cox |
| 5,715,818 A | 2/1998 | Swartz et al. |
| 5,725,553 A | 3/1998 | Moenning |
| 5,755,682 A | 5/1998 | Knudson et al. |
| 5,755,775 A | 5/1998 | Trerotola et al. |
| 5,755,778 A | 5/1998 | Kleshinski |
| 5,758,663 A | 6/1998 | Wilk et al. |
| 5,782,746 A | 7/1998 | Wright |
| 5,797,920 A | 8/1998 | Kim |
| 5,797,934 A | 8/1998 | Rygaard |
| 5,797,960 A | 8/1998 | Stevens et al. |
| 5,799,661 A | 9/1998 | Boyd et al. |
| 5,800,414 A * | 9/1998 | Cazal ............ 604/264 |
| 5,807,243 A | 9/1998 | Vierra et al. |
| 5,807,384 A | 9/1998 | Mueller |
| 5,810,836 A | 9/1998 | Hussein et al. |
| 5,814,005 A | 9/1998 | Barra et al. |
| 5,817,113 A | 10/1998 | Gifford, III et al. |
| 5,824,042 A | 10/1998 | Lombardi et al. |
| 5,824,071 A | 10/1998 | Nelson et al. |
| 5,827,220 A | 10/1998 | Runge |
| 5,829,447 A | 11/1998 | Stevens et al. |
| 5,830,222 A | 11/1998 | Makower |
| 5,830,224 A | 11/1998 | Cohn et al. |
| 5,836,316 A | 11/1998 | Plaia et al. |
| 5,843,088 A | 12/1998 | Barra et al. |
| 5,843,165 A | 12/1998 | Plaia et al. |
| 5,855,210 A | 1/1999 | Sterman et al. |
| 5,855,597 A | 1/1999 | Jayaraman |
| 5,871,536 A | 2/1999 | Lazarus |
| 5,875,782 A | 3/1999 | Ferrari et al. |
| 5,879,321 A | 3/1999 | Hill |
| 5,888,201 A | 3/1999 | Stinson et al. |
| 5,888,247 A | 3/1999 | Benetti |
| 5,893,369 A | 4/1999 | Lemole |
| 5,893,886 A | 4/1999 | Zegdi et al. |
| 5,895,407 A | 4/1999 | Jayaraman |
| 5,897,587 A | 4/1999 | Martakos et al. |
| 5,897,589 A | 4/1999 | Cottenceau et al. |
| 5,899,934 A | 5/1999 | Amundson et al. |
| 5,904,697 A | 5/1999 | Gifford, III et al. |
| 5,908,028 A | 6/1999 | Wilk |
| 5,908,029 A | 6/1999 | Knudson et al. |
| 5,910,168 A | 6/1999 | Myers et al. |
| 5,911,753 A | 6/1999 | Schmitt |
| 5,913,894 A | 6/1999 | Schmitt |
| 5,916,226 A | 6/1999 | Tozzi |
| 5,916,264 A | 6/1999 | Von Oepen et al. |
| 5,922,019 A | 7/1999 | Hankh et al. |
| 5,922,022 A | 7/1999 | Nash et al. |
| 5,925,033 A | 7/1999 | Aita et al. |

| | | | |
|---|---|---|---|
| 5,941,893 A | 8/1999 | Saadat | |
| 5,941,908 A | 8/1999 | Goldsteen et al. | |
| 5,944,019 A | 8/1999 | Knudson et al. | |
| 5,959,995 A | 9/1999 | Wicki et al. | |
| 5,968,089 A | 10/1999 | Krajicek | |
| 5,971,993 A | 10/1999 | Hussein et al. | |
| 5,972,017 A | 10/1999 | Berg et al. | |
| 5,976,178 A | 11/1999 | Goldsteen et al. | |
| 5,980,567 A | 11/1999 | Jordan | |
| 5,984,956 A | 11/1999 | Tweden et al. | |
| 5,989,276 A | 11/1999 | Houser et al. | |
| 5,989,278 A | 11/1999 | Mueller | |
| 5,989,287 A | 11/1999 | Yang et al. | |
| 5,993,489 A | 11/1999 | Lewis et al. | |
| 6,001,124 A | 12/1999 | Bachinski | |
| 6,007,544 A | 12/1999 | Kim | |
| 6,007,576 A | 12/1999 | McClellan | |
| 6,017,352 A | 1/2000 | Nash et al. | |
| 6,019,788 A | 2/2000 | Butters et al. | |
| 6,029,672 A | 2/2000 | Vanney et al. | |
| 6,030,395 A | 2/2000 | Nash et al. | |
| 6,035,856 A | 3/2000 | LaFontaine et al. | |
| 6,036,705 A | 3/2000 | Nash et al. | |
| 6,053,942 A | 4/2000 | Eno et al. | |
| 6,056,762 A | 5/2000 | Nash et al. | |
| 6,063,114 A | 5/2000 | Nash et al. | |
| 6,074,416 A | 6/2000 | Berg et al. | |
| 6,076,529 A | 6/2000 | Vanney et al. | |
| 6,080,163 A | 6/2000 | Hussein et al. | |
| 6,092,526 A | 7/2000 | LaFontaine et al. | |
| 6,093,166 A | 7/2000 | Knudson et al. | |
| 6,102,941 A | 8/2000 | Tweden et al. | |
| 6,113,612 A | 9/2000 | Swanson et al. | |
| 6,123,682 A | 9/2000 | Knudson et al. | |
| 6,139,541 A | 10/2000 | Vanney et al. | |
| 6,143,016 A | 11/2000 | Bleam et al. | |
| 6,148,000 A | 11/2000 | Fedlman et al. | |
| 6,165,185 A | 12/2000 | Shennib et al. | |
| 6,176,864 B1 | 1/2001 | Chapman | |
| 6,179,848 B1 | 1/2001 | Solem | |
| 6,190,397 B1 | 2/2001 | Spence et al. | |
| 6,196,230 B1 | 3/2001 | Hall et al. | |
| 6,197,050 B1 | 3/2001 | Eno et al. | |
| 6,210,430 B1 | 4/2001 | Solem | |
| 6,214,041 B1 | 4/2001 | Tweden et al. | |
| 6,231,587 B1 | 5/2001 | Makower | |
| 6,241,741 B1 | 6/2001 | Duhaylongsod et al. | |
| 6,250,305 B1 | 6/2001 | Tweden | |
| 6,251,104 B1 | 6/2001 | Kesten et al. | |
| 6,251,133 B1 | 6/2001 | Richter et al. | |
| 6,253,768 B1 | 7/2001 | Wilk | |
| 6,253,769 B1 | 7/2001 | LaFontaine et al. | |
| 6,254,564 B1 | 7/2001 | Wilk et al. | |
| 6,293,965 B1 * | 9/2001 | Berg et al. | 623/1.13 |
| 6,325,813 B1 | 12/2001 | Hektner | |
| 6,352,543 B1 | 3/2002 | Cole | |
| 6,402,764 B1 | 6/2002 | Hendricksen et al. | |
| 6,443,158 B1 | 9/2002 | LaFontaine et al. | |
| 6,517,558 B2 | 2/2003 | Gittings et al. | |
| 6,537,288 B2 | 3/2003 | Vargas et al. | |
| 6,635,214 B2 | 10/2003 | Rapacki et al. | |
| 6,651,670 B2 | 11/2003 | Rapacki et al. | |
| 6,652,540 B1 | 11/2003 | Cole et al. | |
| 6,652,541 B1 | 11/2003 | Vargas et al. | |
| 6,669,708 B1 | 12/2003 | Nissenbaum et al. | |
| 6,701,932 B2 * | 3/2004 | Knudson et al. | 128/898 |
| 6,719,768 B1 | 4/2004 | Cole et al. | |
| 6,719,781 B1 | 4/2004 | Kim | |
| 6,802,847 B1 | 10/2004 | Carson et al. | |
| 6,808,498 B2 | 10/2004 | Laroya et al. | |
| 6,955,679 B1 | 10/2005 | Hendricksen et al. | |
| 7,017,581 B2 | 3/2006 | Boyd et al. | |
| 7,025,773 B2 | 4/2006 | Gittings et al. | |
| 7,027,398 B2 | 4/2006 | Fang et al. | |
| 7,041,110 B2 | 5/2006 | Yencho et al. | |
| 7,137,962 B2 | 11/2006 | Gittings et al. | |
| 7,214,234 B2 | 5/2007 | Rapacki et al. | |
| 7,285,235 B2 | 10/2007 | Rapacki et al. | |
| 2001/0004699 A1 | 6/2001 | Gittings et al. | |
| 2001/0025643 A1 | 10/2001 | Foley | |
| 2001/0041902 A1 | 11/2001 | Lepulu et al. | |
| 2002/0004663 A1 | 1/2002 | Gittings et al. | |
| 2002/0077566 A1 | 6/2002 | Laroya et al. | |
| 2002/0144696 A1 | 10/2002 | Sharkawy et al. | |
| 2002/0161424 A1 | 10/2002 | Rapacki et al. | |
| 2002/0193782 A1 | 12/2002 | Ellis et al. | |
| 2003/0158573 A1 | 8/2003 | Gittings et al. | |
| 2004/0077987 A1 | 4/2004 | Rapacki et al. | |
| 2004/0097988 A1 | 5/2004 | Gittings et al. | |
| 2004/0113306 A1 | 6/2004 | Rapacki et al. | |
| 2004/0134487 A1 | 7/2004 | Deem et al. | |
| 2004/0154621 A1 | 8/2004 | Deem et al. | |
| 2004/0167444 A1 | 8/2004 | Laroya et al. | |
| 2004/0168691 A1 | 9/2004 | Sharkawy et al. | |
| 2005/0043781 A1 | 2/2005 | Foley | |
| 2005/0051163 A1 | 3/2005 | Deem et al. | |
| 2005/0192604 A1 | 9/2005 | Carson et al. | |
| 2007/0055344 A1 | 3/2007 | Gittings et al. | |
| 2007/0233225 A1 | 10/2007 | Rapacki et al. | |

FOREIGN PATENT DOCUMENTS

| | | |
|---|---|---|
| EP | 0515867 | 12/1992 |
| EP | 0834287 | 4/1998 |
| GB | 2316322 | 2/1998 |
| SU | 736966 | 5/1980 |
| SU | 1179978 | 9/1985 |
| SU | 1754128 | 8/1992 |
| WO | WO 82/01644 | 5/1982 |
| WO | WO 84/02266 | 6/1984 |
| WO | WO 88/06865 | 9/1988 |
| WO | WO 90/15582 | 12/1990 |
| WO | WO 92/16141 | 10/1992 |
| WO | WO 93/00868 | 1/1993 |
| WO | WO 94/21197 | 9/1994 |
| WO | WO 95/33407 | 12/1995 |
| WO | WO 95/35065 | 12/1995 |
| WO | WO 96/00033 | 1/1996 |
| WO | WO 96/04854 | 2/1996 |
| WO | WO 96/04865 | 2/1996 |
| WO | WO 96/05773 | 2/1996 |
| WO | WO 96/22745 | 8/1996 |
| WO | WO 97/12555 | 4/1997 |
| WO | WO 97/13463 | 4/1997 |
| WO | WO 97/13471 | 4/1997 |
| WO | WO 97/27893 | 8/1997 |
| WO | WO 97/27897 | 8/1997 |
| WO | WO 97/27898 | 8/1997 |
| WO | WO 97/31464 | 8/1997 |
| WO | WO 97/32545 | 9/1997 |
| WO | WO 97/36453 | 11/1997 |
| WO | WO 98/06356 | 2/1998 |
| WO | WO 98/08456 | 3/1998 |
| WO | WO 98/16161 | 4/1998 |
| WO | WO 98/16174 | 4/1998 |
| WO | WO 98/19608 | 5/1998 |
| WO | WO 98/19614 | 5/1998 |
| WO | WO 98/19629 | 5/1998 |
| WO | WO 98/19630 | 5/1998 |
| WO | WO 98/19631 | 5/1998 |
| WO | WO 98/19634 | 5/1998 |
| WO | WO 98/19635 | 5/1998 |
| WO | WO 98/19636 | 5/1998 |
| WO | WO 98/23241 | 6/1998 |
| WO | WO 98/38939 | 9/1998 |
| WO | WO 98/38941 | 9/1998 |
| WO | WO 98/38942 | 9/1998 |
| WO | WO 98/38947 | 9/1998 |
| WO | WO 98/46115 | 10/1998 |
| WO | WO 98/46119 | 10/1998 |
| WO | WO 98/49964 | 11/1998 |
| WO | WO 98/55027 | 12/1998 |
| WO | WO 98/57590 | 12/1998 |
| WO | WO 98/57591 | 12/1998 |
| WO | WO 98/57592 | 12/1998 |
| WO | WO 99/17683 | 4/1999 |
| WO | WO 99/18887 | 4/1999 |
| WO | WO 99/21490 | 5/1999 |
| WO | WO 99/22658 | 5/1999 |

| | | |
|---|---|---|
| WO | WO 99/25273 | 5/1999 |
| WO | WO 99/36000 | 7/1999 |
| WO | WO 99/36001 | 7/1999 |
| WO | WO 99/37349 | 7/1999 |
| WO | WO 99/38441 | 8/1999 |
| WO | WO 99/38454 | 8/1999 |
| WO | WO 99/38459 | 8/1999 |
| WO | WO 99/40868 | 8/1999 |
| WO | WO 99/48545 | 9/1999 |
| WO | WO 99/49793 | 10/1999 |
| WO | WO 99/49910 | 10/1999 |
| WO | WO 99/51162 | 10/1999 |
| WO | WO 99/53863 | 10/1999 |
| WO | WO 99/60941 | 12/1999 |
| WO | WO 99/62430 | 12/1999 |
| WO | WO 99/63910 | 12/1999 |
| WO | WO 99/65409 | 12/1999 |
| WO | WO 00/12020 | 3/2000 |
| WO | WO 00/15146 | 3/2000 |
| WO | WO 00/15147 | 3/2000 |
| WO | WO 00/15148 | 3/2000 |
| WO | WO 00/15149 | 3/2000 |
| WO | WO 00/15275 | 3/2000 |
| WO | WO 00/21436 | 4/2000 |
| WO | WO 00/24449 | 5/2000 |
| WO | WO 00/41633 | 7/2000 |
| WO | WO 00/21461 | 9/2000 |
| WO | WO 00/69364 | 11/2000 |
| WO | WO 00/74579 | 12/2000 |
| WO | WO 01/17440 | 3/2001 |
| WO | WO 01/39672 | 6/2001 |
| WO | WO 00/41633 | 7/2001 |

OTHER PUBLICATIONS

Ahmed, et al., Silent Left Coronary Artery—Cameral Fistula: Probably Cause of Myocardial Ischemia; *Amer. Heart J.*, 1982, 104(4):869-870.

Ahn CY, Shaw WW, Berns S, et al., "Clinical Experience With the 3M Microvascular Coupling Anastomotic Device in 100 Free-Tissue Transfers," *Plastic and Reconstructive Surgery*, Jun. 1994; 93(7):1481-1484.

Andrews et al., Assessment of Feasibility for Endovascular Prosthetic Tube Correction of Aortic Aneurysm, *Brit. J. Surg.*, 1995, 82:917-919.

Antonatos, et al., Effect of the Positioning of a Balloon Valve in the Aorta on Coronary Flow during Aortic Regurgitation, *J. Thorac. Cardiovas. Surg.*, Jul. 1984;88(1):128-133.

Arani, D., et al., Coronary Artery Fistulas Emptying into Left Heart Chamber, *Amer. Heart J.*, 1978; 96(4):438-443.

Arom, et al., Patient Characteristics, Safety, and Benefits of Same-Day Admission for Coronary Artery Bypass Grafting, *Ann. Thorac. Surg.*, 1996, 61:1136-1140.

Attai, et al, Aortic Valve Replacement in the Presence of Hufnagel Valve in the Descending Aorta, *J. Thoracic Cardiovas. Surg.*, 1974, 68(1):112-115.

Baird, et al., Intramyocardial Pressure, A Study of its Regional Variations and its Relationship to Intraventricular Pressure, *Journal of Thoracic and Cardiovascular Surgery*, vol. 59, No. 6, Jun. 1970, pp. 810-823.

Beppu, et al., A Computerized Control System for Cardiopulmonary Bypass, *J. Thoracic Cardiovas. Surg.*, 1995, 109(3):428-438.

Beyar, R., et al., Self-Expandable Nitinol Stent for Cardiovascular Applications, *Catheterization and Cardiovascular Diagnosis*, 1994; 32:162-170.

Binns, RL., et al., Optimal Graft Diameter: Effect of Wall shear Stress on Vascular Healing, *J. Vasc. Surg.*, 1989; 10(3):326-337.

Black, et al., Multiple Coronary Artery—Left Ventricular Fistulae: Clinical, Angiographic, and Pathologic Findings, *Cath. Cardio. Diag.*, 1991, 23:133-135.

Borst, C., et al., Coronary Artery Bypass Grafting Without Cardiopulmonary Bypass and Without Interruption of Native Coronary Flow Using a Novel Anastomosis Site Restraining Device ("Octopus "), *J. Am. Coll. Cardiol.*, 1996; 27:1356-64.

Buckberg, G.D., Update on Current Techniques of Myocardial Protection, *Society Thorac. Surgeons*, 1995, 60:805-814.

Buffolo, et al., Coronary Artery Bypass Grafting without Cardiopulmonary Bypass, *Ann. Thorac. Surg.*, 1996, 61:63-66.

Butterfield, AB, et al., Inverse Effect of Chronically Elevated Blood Flow on Atherogenesis in Miniature Swine, *Atherosclerosis*, 1977; 26:215-224.

Cale, AJ, et al., Hufnagel Revisited: A Descending Thoracic Aortic Valve to Treat Prosthetic Valve Insufficiency, *Ann. Thorac. Surg.*, 1993; 55:1218-21.

Campbell, CD, et al., A Small Arterial Substitute: Expanded Microporous Polytetrafluoroethylene: Patency Versus Porosity, *Ann. Surg.* 1975; 182:138-143.

Campeau, L., et al., Postoperative Changes in Aortocoronary Saphenous Vein Grafts Revisited, *Circulation*, 1975; 52:369-377.

Candinas, R., et al., Postmortem Analysis of Encapsulation Around Long-Term Ventricular Endorcardial Pacing Leads, *Mayo Clin. Proc.*, 1999; 74:120-125.

Cercek, et al., Growth Factors in Pathogenesis of Coronary Arterial Restenosis, *Amer. J. Cardio.*, 1991, 68:24C-33C.

Cha, et al., Silent Coronary Artery—Left Ventricular Fistula: a Disorder of the Thebesian System?, Angiology, 1978; 29(2):169-173.

Cha, S.D., Coronary Artery to Left Ventricular Fistula, *Catheterization Cardio. Diag.*, 1991, 24:150.

Cheng, et al., Traumatic Aneurysm of Left Anterior Descending Coronary Artery with Fistulous Opening into Left Ventricle and Left Ventricular Aneurysm after Stab Wound of Chest, *Amer. J. Card.*, 1973, 31:384-390.

Cheng, To.O., Left Coronary Artery-to-Left Ventricular Fistula: Demonstration of Coronary Steal Phenomenon, *Amer. Heart J.*, 1982, 104(4):870-872.

Chia, et al., Coronary Artery—Left Ventricular Fistula, *Cardiology*, 1981, 68:167-179.

Connolly, et al., Cardiopulmonary Bypass and Intraoperative Protection, *Heart Arteries Veins*, 1994, 141:2443-2450.

Cooley, et al., Surgical Considerations of Coronary Arterial Fistula, *Am. J. Cardiol.*, 1962, 10(4):467-474.

Cooper, CL and Miller A., Infectious Complications Related to the Use of the Angio-Seal Hemostatic Puncture Closure Device, *Catheterization and Cardiovascular Interventions*, 1999;.48:301-303.

Cuadros, L., One Hundred Percent Patency of One-Millimeter Polytetrafluoroethylene (Gore-Tex) Grafts in the Carotid Arteries of Rats, *Microsurgery*, 1984; 5:1-11.

Dake, et al., Transluminal Placement of Endovascular Stent-Grafts for the Treatment of Descending Thoracic Aortic Aneurysms, *New England J. Med.*, 1994, 331(26):1729-1.

Daniel, RK, et al., An Anastomotic Device for Microvascular Surgery: Evolution, *Annals of Plastic Surgery*, 1984; 13(5):402-411.

DeLacure, MD, et al., Clinical Experience in End-to-Side Vernous Anastomoses With a Microvascular Anastomotic Coupling Device in Head and Neck Reconstruction, *Arch. Otolaryngol. Head Neck Surg.*, 1999; 125:869-872.

Dolmatch, BL, et al., Tissue Response to Covered Wallstents, JVIR, 1998; 9(3):471-478.

du Plessis, et al., Aortic Valve Replacement in the Presence of a Hufnagel Valve Prosthesis, *J. Thoracic Cardiovs. Surg.*, 1996, 51(4):493-497.

Elian, D., Left Coronary Artery to Left Ventricular Fistual Can Result in a Coronary Steal, *Catheterization Cardiovas. Diag.*, 1998, 43:490.

Emery, RW, et al., Operative Considerations in Implantation of the Perma-Flow Graft, *Ann. Thorac. Surg.*, 1994; 58:1770-73.

Emery, RW, et al., North American Experience With the Perma-Flow Prosthetic Coronary Graft, *Ann. Thorac. Surg.*, 1996; 62:691-96.

Emery, RW, et al., First Clinical Use of the Possis Synthetic Coronary Graft, *J. Card. Surg.*, 1993; 8:439-442.

Esquivel, CO, et al., Reduced Thrombogenic Characteristics of Expanded Polytetrafluoroethylene and Polyurethane Arterial Grafts After Heparin Bonding, *Surgery*, 1984; 95(1):102-107.

Flynn, et al., Does systolic Subepicardial Perfusion come from Retrograde Subendocardial Flow?, *Amer. Physiological Society*, 1992, 262: pp. 1759-1769.

Galioto, FM, et al., Right Coronary Artery to Left Ventricle Fistula, *Amer. Heart J.*, 1971; 82(1):93-97.

Gentile, AT, et al., Vein Patching Reduces Neointimal Thickening Associated with Prosthetic Graft Implantation, *Am. J. Surg.*, 1998; 176:601-607.

Gitter, et al., Influence of Ascending Versus Descending Balloon Counterpulsation on Bypass Graft Blood Flow, *Ann. Thorac. Surg.*, 1998, 65:365-370.

Goldman, et al., Experimental Methods for Producing a Collateral Circulation to the Heart Directly from the Left Ventricle, *J. Thoracic Surg.*, 1956, 31(3):364-374.

Green, et al., The Phasic Changes in Coronary Flow Established by Differential Pressure Curves, *Department of Physiology, Western Reserve University*, Cleveland, Ohio, May 6, 1935, pp. 627-639.

Gregg, et al., Measurements of Intramyocardial Pressure, *Department of Medicine, Western Reserve University School of Medicine*, Cleveland, Ohio, Oct. 21, 1940, pp. 781-790.

Guyton, RA, et al., A Mechanical Device for Sutureless Aorta-Saphenous Vein Anastomosis, *Ann. Thoracic Surg.*, 1979; 28(4):342-345.

Halkier, et al., Aortic Incompetence: The Eventual Outcome in a Small Series Treated with Hufnagel's Descending Aorta Ball-valve, *Scand. J. Thor. Cardiovasc. Surg.*, 1970, 4:52-55.

Harada, et al., VEGF in Chronic Myocardial Ischemia, *Amer. Physiol. Soc.*, 1996, H1791-H1801.

Haravon, et al., Congenital Coronary Artery to Left Ventricle Fistula with Angina Pectoris, *N.Y. State J. Med.*, 1972, pp. 2196-2200.

Hausdorf, et al., Radiofrequency-assisted "Reconstruction" of the Right Ventricular Outflow Tract in Muscular Pulmonary Atresia with Ventricular Septal Defect, *Br. Heart J.*, 1993, 69:343-346.

Heijmen, RH, et al., Temporary Luminal Arteriotomy Seal: II. Coronary Artery Bypass Grafting on the Beating Heart, *Ann. Thorac. Surg.*, 1998; 66:471-476.

Hofma, et al., Increasing Arterial Wall Injury after Long-term Implantation of Two Types of Stent in a Porcine Coronary Model, *Eur. Heart. J.*, 1998, 19:601-609.

Hongo, et al., Effects of Heart Rate on Phasic Coronary Blood Flow Pattern and Flow Reserve in Patients with Normal Coronary Arteries: A Study with an Intravascular Doppler Catheter and Spectral Analysis, *Amer. Heart J.*, 1994, 127(3):545-551.

Houki, et al., A Stimulation Study of Coronary Circulatory System, *Jap. Cir. J.*, 1977, 41:1279-1280.

Hufnagel, et al., Surgical Correction of Aortic Insufficiency, *Surgery*, 1954, 35(5):673-683.

Hutchins, et al., Aterial-venous Relationships in the Human Left Ventricular Myocardium, Anatomoic Basis for Countercurrent Regulation of Blood Flow, *Circulation*, vol. 74, No. 6, Dec. 1986, pp. 1195-1202.

Ilia, R., Coronary Angiography in Dextrocardia, *Catheterization Cardio. Diag.*, 1991, 24 p. 150.

Jamieson, S.W., Aortocoronary Saphenous Vein Bypass Grafting, *Operative Surgery*, 4th Edition, pp. 454-470.

Kaiser, et al., Video-Assisted Thoracic Surgery: The Current State of the Art, *AJR*, 1995, 165:1111-1117.

Kajiya, et al., Endocardial Coronary Microcirculation of the Beating Heart, *Interactive Phenomena in the Cardiac System*, 1993, pp. 173-180.

Kajiya, et al., Mechanical Control of Coronary Artery Inflow and Vein Outflow, *Jap. Cir. J.*, 1989, 53:431-438.

Kajiya, et al., Velocity Profiles and Phasic Flow Patterns in the Nonstenotic Human Left Anterior Descending Coronary Artery During Cardiac Surgery, *Cardiovasc. Research*, 1993, 27:845-850.

Kohmoto, et al., Does Blood Flow through Holmium: YAG Transmyocardial Laser Channels?, *Ann. Thorac. Surg.*, 1996, 61:861-868.

Koyama, T el al., Non-uniform Oxygen Supply to the Left Ventricular Myocardium by Systolic Perfusion of Coronary Artery, Japanese J of Physiology, 1979, 29, 267-274.

Louagie et al., Operative Risk assessment in Coronary Artery Bypass Surgery, 1990-1993 : Evaluation of Perioperative Variables, *Thorac. Cardiovasc. Surg.*, 1995; 43:134-141.

Marin, et al., Initial Experience with Transluminally Placed Endovascular Grafts for the Treatment of Complex Vascular Lesions, *Annals of Surg.*, 1995, 222(4):449469.

Massimo, et al., Myocardial Revascularization by a New Method of Carrying Blood Directly from the Left Ventricular Cavity into the Coronary Circulation, *Journal of Thoracic and Cardiovascular Surgery*, vol. 34, No. 2, Aug. 1957, pp. 257-265.

Matsumae M et al., An Experimental Study of New Sutureless Intraluminal Graft With an Elastic Ring That Can Attach Itself to the Vessel Wall, *J. Vasc. Surg.*, 1988;8:33-44.

McLellan BA et al., Myocardial Infarction Due to Multiple Coronary—Ventricular Fistulas. *Catheterization and CardioVascular Diagnosis*, 1989;16:247-249.

McNamara, et al., Congenital Coronary Artery Fistula, *Surgery*, 1969, 65(1):59-69.

Midell, et al., Surgical Closure of Left Coronary Artery—Left Ventricular Fistula, *J. Thorac. Cardiovas. Surg.*, 1997, 2:199-203.

Milano, et al., Mediastinitis after Coronary Artery Bypass Graft Surgery, *Circulation*, 1995, 92(8):2245-2251.

Mirhoseini, et al., Myocardial Revascularization by Laser: A Clinical Report, *Lasers in Surg. Med.*, 1983, 3:241-245.

Mirhoseini, et al., New Concepts in Revascularization of the Myocardium, *Ann. Thorac. Surg.*, 1988, 45:415-420.

Munro, et al., The Possibility of Myocardial Revascularization by Creation of a Left Ventriculocoronary Artery Fistula, *Journal of Thoracic and Cardiovascular Surgery*, vol. 58, No. 1, Jul. 1969, pp. 25-32.

Nishida, et al., Flow Study of Surgical Coronary Artery Fistula as an Alternative to Sequential Bypass, *Cariovascular Surg.*, 1995, 3(4):375-380.

Nollert, et al., Use of the Internal Mammary Artery as a Graft in Emergency Coronary Artery Bypass Grafting after Failed PTCA, *Thorac. Cardiovasc. Surg.*, 1995, 43:142-147.

O'Connor, et al., Ventriculocoronary Connections in Hypoplastic Left Hearts: An Autopsy Microscopic Study, *Circulation*, 1982, 66(5):1078-1086.

Obora, et al., Nonsuture Microvascular Anastomosis Using Magnet Rings, Neurol. Med. Chir., 1980, 20: pp. 497-505.

Obora, et al., Nonsuture Microvascular Anastomosis Using Magnet Rings: Preliminary Report, *Surg. Neurol*—1978 vol. 9: 117-120.

Okuda, et al., Right Coronary Artery to Left Ventricle Fistula, *Jap. Heart J.*, 1973, 14(2):184-191.

Pelletier, et al., Angiogenesis and Growth Factor Expression in a Model of Transmyocardial Revascularization, *Ann of Thorac. Surg.*, 1998, 66:12-18.

Petropoulakis, et al., *Changes in Phasic Coronary Blood Flow Velocity Profile in Relation to Changes in Hemodynamic Parameters during Stress in Patients with Aortic Valve Stenosis*, Circulation, 1995, 92(6):1437-1447.

Pifarre, et al., Myocardial Revascularization by Transmyocardial Acupuncture, A Physiologic Impossibility, *Journal of Thoracic and Cardiovascular Surgery*, vol. 58, No. 3, Sep. 1969, pp. 424-431.

Pifarre, et al., Myocardial Revascularization from the Left Ventricle: A Physiological Impossibility, *Surgical Forum*, 1968, 19:157-159.

Reddy, et al., Multiple Coronary Arteriosystemic Fistulas, *Amer. J. Cardiol.*, 1974, 33:304-306.

Roe, et al., Experimental Results with a Prosthetic Aortic Valve, *J. Thoracic Surg.*, 1958, 36(4):563-570.

Roe, et al., The Subcoronary Implantation of a Flexible Triscupid Aortic Valve Prosthesis, *J. Thorac. Cardiovs. Surg.*, 1960, 40(5):561-567.

Ryan, et al., Fistula from Coronary Arteries to Left Ventricle after Myocardial Infarction, *Brit. Heart J.*, 1977, 39:1147-1149.

Salzmann, DL, et al., Effects of Balloon Dilatation on ePTFE Structural Characteristics, *J. Biomed. Mater. Res.*, 1997; 36:498-507.

Salzmann, DL, et al., Healing Response Associated with Balloon-dilated ePTFE, *J. Biomed. Mater. Res.*, 1998; 41:364-370.

Sastri, et al., Coronary Artery Left Ventricular Fistula, *Chest*, 1975, 68(5):735-736.

Scheltes, et al., Assessment of Patented Coronary End-to-Side Anastomotic Devices Using Micromechanical Bonding, *Ann. Thorac. Surg.*, 2000, 70:218-221.

Schneider, t al., Transcatheter Radiofrequency Perforation and Stent Implantation for Palliation of Pulmonary Atresiain a 3060-g Infant, *Catheterization Cardiovas. Diag.*, 1995, 34:42-45.

Schwartz, et al., Minimally Invasive Cardiopulmonary Bypass with Cardioplegic Arrest: A Closed Chest Technique with Equivalent Myocardial Protection, *J. Thorac. Cardiovasc. Surg.*, 1996, 111:556,566.

Segal, et al., Alterations of Phasic Coronary Artery Flow Velocity in Humans During Percutaneous Coronary Angioplasty, *JACC*, 1992, 20(2):276-286.

Sen, et al., Transmyocardial Acupuncture, A New Approach to Myocardial Revascularization, *Journal of Thoracic and Cardiovascular Surgery*, vol. 50, No. 2, Aug. 1965, pp. 181-189.

Sheikhzadeh A et al., Generalized Coronary Arterio-Systemic (left ventricular)fistula. *Jpn. Heart J.*, 1986;27(4:533-544.

Sigwart, U., *An Overview of Intravascular Stents: Old and New*, pp. 803-815.

Silvay, et al., Cardiopulmonary Bypass for Adult Patients: A Survey of Equipment and Techniques, *J. Cardiothoracic Vas. Anetsh.*, 1995, 9(4):420-424.

Stefanadis, C., et al., Stents Covered by an Autologous Arterial Graft in Porcine Coronary Arteries: Feasibility, Vascular Injury and Effect on Neointimal Hyperplasia, *Cardiovascular Research*, 1999; 41:433-442.

Stevens, et al., Port-Access Coronary Artery Bypass Grafting: A Proposed Surgical Method, *J. Thorac. Cardiovasc. Surg.*, 1996, 111(3):567-573.

Taylor, KM, Brain Damage During Cardiopulmonary Bypass, *Ann. Thorac. Surg.*, 1998; 65:S20-6.

Vierra, M., Minimally Invasive Surgery, *Annu. Rev. Med.*, 1995, 46:147-158.

Vineberg, Coronary Vascular Anastomoses by Internal Mammary Artery Implantation, *Review Article*, vol. 78, Jun. 1, 1958, pp. 871-879.

Vineberg, et al., Treatment of Acute Myocardial Infarction by Endocardial Resection, *Surgery*, 1965, 57(6):832-835.

von Segesser, L.K., *Arterial Grafting for Myocardial Revascularization*, 1990, pp. 3-140.

Vongpatanasin, et al., Prosthetic Heart Valves, *New England J. Medicine*, 1996, 335(6):407-416.

Waller, et al., The Pathology of Interventional Coronary Artery Techniques and Devices, *Topol's Texbook of Interventional Cardiology 1994* pp. 449-476.

Wearn, et al., The Nature of the Vascular Communications Between the Coronary Arteries and the Chambers of the Heart, *The American Heart Journal*, vol. IX, No. 2, Dec. 1933, pp. 143-164.

Whittaker, et al., Transmural Channels Can Protect Ischemic Tissue, *Circulation*, 1996, 93(1):143-152.

Wolfe, et al., Fistules Coronaro-Ventriculaires Gauches, *Mal. Coéur.*, 1981, 74(11):1353-1357.

\* cited by examiner

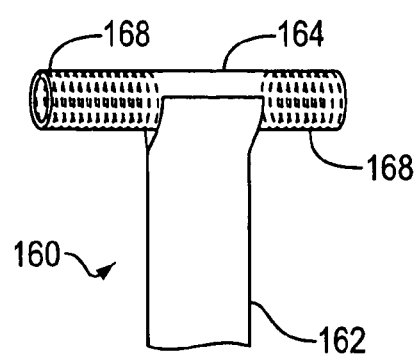
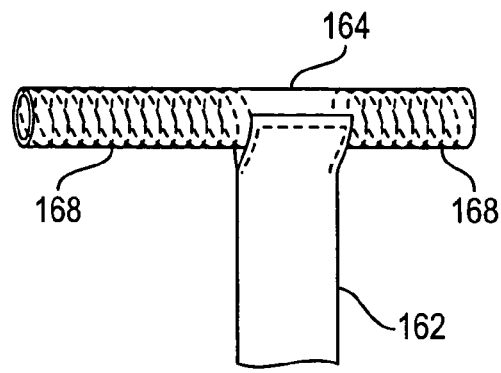
FIG. 13A
FIG. 13B
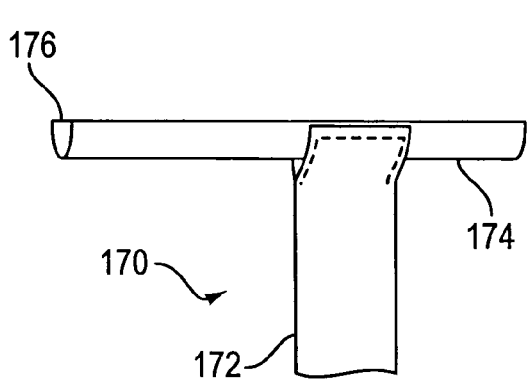
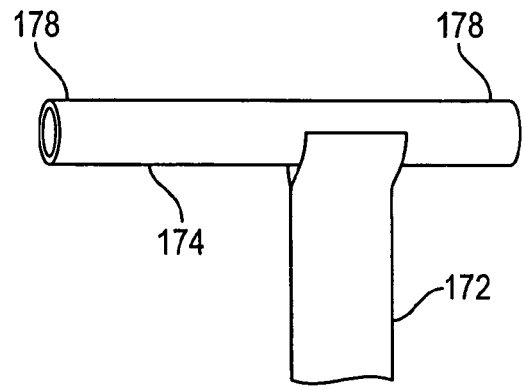
FIG. 14A
FIG. 14B
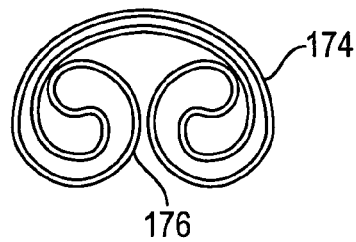
FIG. 14C

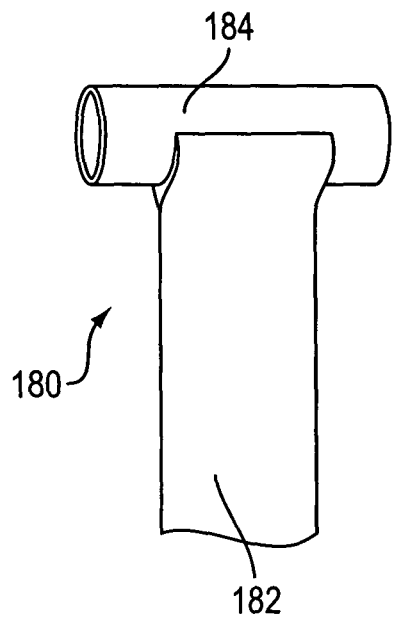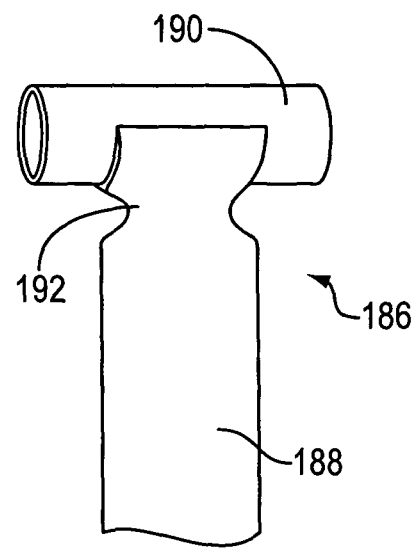
FIG. 15        FIG. 16
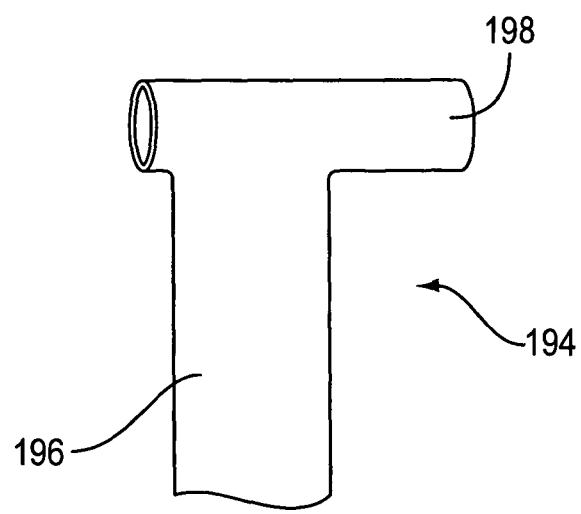
FIG. 17

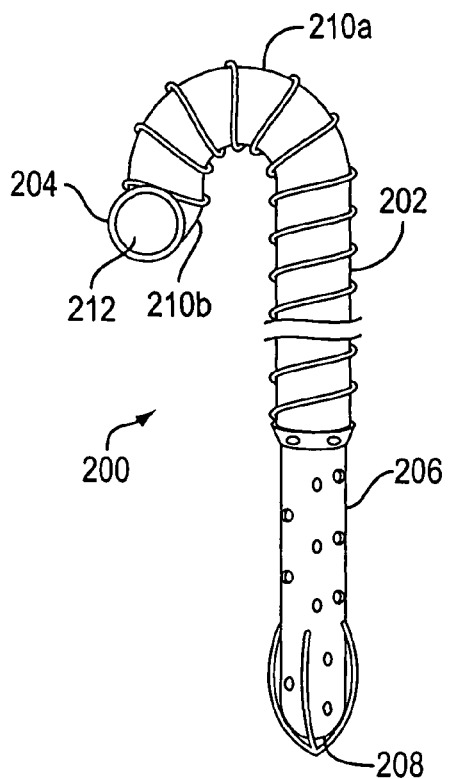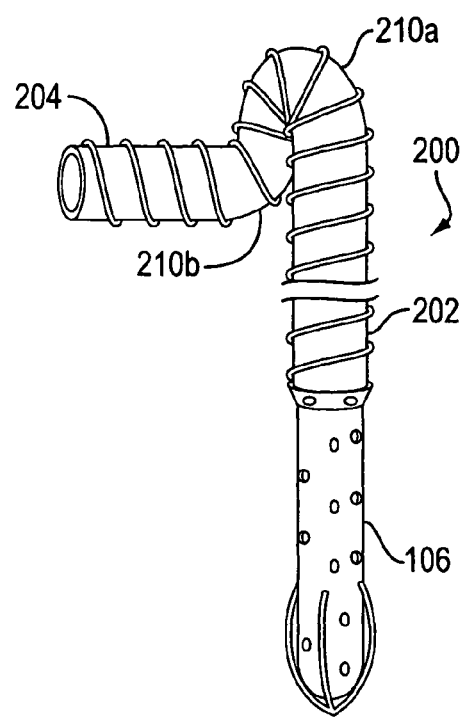
FIG. 18A  FIG. 18B
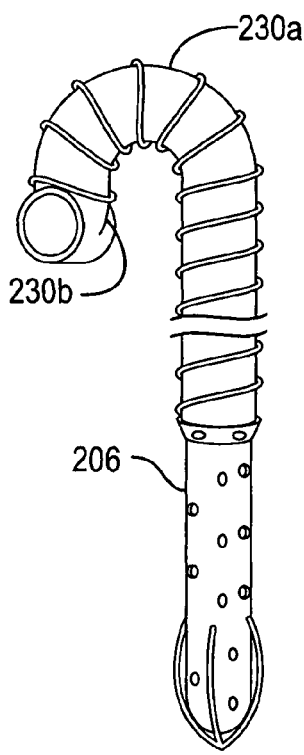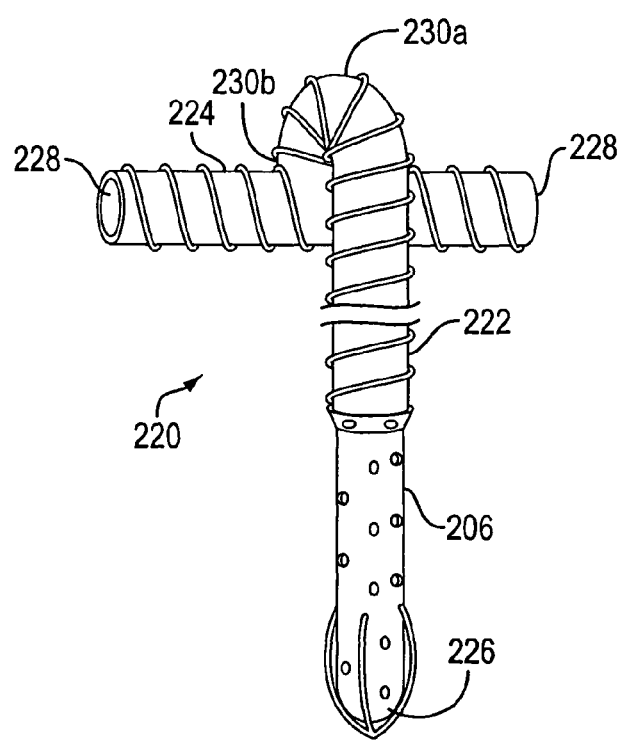
FIG. 19A  FIG. 19B

CONDUITS FOR USE IN PLACING A TARGET VESSEL IN FLUID COMMUNICATION WITH SOURCE OF BLOOD

CROSS-REFERENCES TO RELATED APPLICATIONS

This application is a continuation application of application Ser. No. 09/393,131, filed on Sep. 10, 1999, now abandoned which is a continuation-in-part of application Ser. No. 09/023,492, filed on Feb. 13, 1998, now abandoned application Ser. No. 09/232,103, filed on Jan. 15, 1999 now abandoned and application Ser. No. 09/232,062, filed on Jan. 15, 1999, now abandoned the entire disclosures of which are hereby incorporated by reference.

BACKGROUND OF THE INVENTION

1. Field of the Invention

The invention relates to a conduit that is placed in fluid communication with a target vessel and a source of blood, and methods and devices for placing the conduit in fluid communication with the target vessel and the source of blood.

2. Description of the Background Art

Despite the considerable advances that have been realized in cardiology and cardiovascular surgery, heart disease remains the leading cause of death throughout much of the world. Coronary artery disease, or arteriosclerosis, is the single leading cause of death in the United States today. As a result, those in the cardiovascular field continue to search for new and improved treatments.

Coronary artery disease is currently treated by interventional procedures such as percutaneous transluminal coronary angioplasty (PTCA), coronary stenting and atherectomy, as well as surgical procedures including coronary artery bypass grafting (CABG). The goal of these procedures is to reestablish or improve blood flow through occluded (or partially occluded) coronary arteries, and is accomplished, for example, by enlarging the blood flow lumen of the artery or forming a bypass that allows blood to circumvent the occlusion. What procedure(s) is used typically depends on the severity and location of the blockage(s). When successful, these procedures restore blood flow to myocardial tissue that had not been sufficiently perfused due to the occlusion.

An alternative, recently proposed treatment places the target vessel in fluid communication with a heart chamber containing blood, for example, the left ventricle. Blood flows from the ventricle into a conduit that is in fluid communication with the target vessel. Some of the challenges associated with these procedures include delivering and deploying the conduit in the patient's body, and in particular properly positioning the conduit with respect to the heart chamber and the target vessel, as well as obtaining beneficial flow characteristics through the target vessel.

The improvement and refinement of existing treatments and the search for new treatments are indicative of the significant effort that continues to be expended in order to develop better and more efficient ways of revascularizing the heart.

Accordingly, there remains a need in the art for improved methods and devices that are capable of being used quickly, easily and in a repeatable manner to carry out cardiac revascularization.

SUMMARY OF THE INVENTION

The invention provides methods and devices for placing a conduit in fluid communication with a source of blood and a target vessel. One preferred method according to the invention includes steps of placing a conduit having a lumen in fluid communication with a heart chamber containing blood, placing the conduit in fluid communication with the lumen of a target vessel and securing the conduit to the target vessel, delivering blood from the heart chamber into the conduit during at least one phase of the heart cycle, and permitting the blood to flow from the conduit into the lumen of the target vessel in more than one direction.

Another preferred method is similar to the above-described method but includes the additional step of permitting the blood to exit the conduit unrestricted and in more than one direction in the lumen of the target vessel.

Another preferred method includes steps of providing a conduit including first and second portions that are disposed transverse to each other and have lumens in fluid communication, the first conduit portion including at least one inlet and the second conduit portion including at least one outlet. The inlet of the first conduit portion is placed in fluid communication with a heart chamber containing blood to allow blood to enter the lumen of the first conduit portion, and the outlet of the second conduit portion is placed in fluid communication with the lumen of a target vessel at a selected location in the target vessel to allow blood to flow into the lumen of the target vessel from the second conduit portion. The second conduit portion is secured to the target vessel at the selected location while substantially not moving the second conduit portion along a longitudinal axis of the target vessel.

Still another preferred method includes steps of providing a conduit including first and second portions each of which has a lumen, wherein the first and second conduit portions are disposed transverse to each other with the lumens in fluid communication and the second conduit portion is at least partially collapsible, and placing the lumen of the first conduit portion in fluid communication with a heart chamber containing blood. The second conduit portion is at least partially collapsed and positioned within the lumen of a target vessel at a selected location in the target vessel, and is then expanded within the target vessel lumen at the selected location to secure the second conduit portion to the target vessel in fluid communication therewith.

Yet another preferred method includes steps of determining a thickness of the patient's myocardium adjacent a heart chamber containing blood, placing a conduit having a lumen in the myocardium with the lumen of the conduit in fluid communication with the heart chamber containing blood, placing the conduit in fluid communication with the lumen of a target vessel and securing the conduit to the target vessel, and delivering blood from the heart chamber into the conduit and allowing blood to exit the conduit and enter the target vessel in more than one direction.

One preferred device constructed according to the invention includes a conduit having first and second portions, wherein the first and second conduit portions each have an axis and a lumen through which blood may flow, the axes of the first and second conduit portions being transverse to each other. The first conduit portion is configured to be placed in fluid communication with a heart chamber containing blood and includes at least one inlet configured to be at least partially positioned in myocardial tissue without collapsing during myocardial contraction, whereas the second conduit portion is configured to be at least partially positioned within the target vessel and includes at least one outlet adapted to deliver blood to the target vessel. The inlet of the first conduit portion is more rigid than the outlet of the second conduit portion.

Another preferred device includes a conduit having first and second portions that are transverse to each other and have lumens in fluid communication. The first conduit portion has a longitudinal axis and is sized and configured to be placed in fluid communication with a heart chamber containing blood, and the second conduit portion has a longitudinal axis and is sized and configured to be placed at least partially within a target vessel in a patient's vascular system to deliver blood to the target vessel. The second conduit portion has first and second ends adapted to be positioned in the target vessel, and the longitudinal axis of the first conduit portion crosses the longitudinal axis of the second conduit portion at a location that is spaced different distances from the first and second ends of the second conduit portion.

Another preferred device includes a conduit having first and second portions having respective axes that are transverse to each other, the first conduit portion having a free end configured to be placed in fluid communication with a heart chamber containing blood, and the second conduit portion having two free ends that are configured to be positioned at least partially within the lumen of a target vessel in the patient's vascular system. The conduit is formed at least in part of a molded thermoset or thermoplastic material having a predetermined amount of flexibility to permit the second portion of the conduit to be flexed for placement within the lumen of a target vessel.

The invention also provides devices and methods for delivering a conduit configured to be placed in fluid communication with a target vessel and a source of blood. One preferred delivery device includes a support shaft having a length, and a sheath having a length, a lumen, and a wall with at least one opening extending into the sheath lumen. The support shaft is sized and configured to be at least partially positioned in the sheath lumen so as to contact the sheath wall and substantially block the opening by preventing communication with the sheath lumen via the opening. The support shaft is movable within the sheath lumen to selectively block or unblock the opening in the sheath wall. A conduit is placed on the sheath and, with the opening unblocked, delivers blood into the sheath lumen for perfusing a vessel into which the distal end of the sheath is positioned. As a result, the device may be used to deliver blood to the tissue during deployment of the conduit, thereby minimizing ischemic time for tissue that heretofore was not perfused while carrying out the procedure.

Another preferred delivery device is adapted to deliver a conduit for placing a target vessel in fluid communication with a source of blood, the conduit including first and second transverse portions each of which has an axis and a lumen. The first conduit portion includes at least one inlet configured to be placed in fluid communication with a heart chamber containing blood, and the second conduit portion includes at least one outlet configured to be at least partially positioned within the lumen of a target vessel to deliver blood to the target vessel. The delivery device includes a shaft with a lumen and at least one opening extending into the lumen, and the second conduit portion is mounted on the shaft. The shaft opening is movable into and out of alignment with the lumen of the first conduit portion, and is moved into alignment with the lumen of the first conduit portion to deliver blood to the shaft lumen.

BRIEF DESCRIPTION OF THE DRAWINGS

The invention will be better understood from the following detailed description of preferred embodiments thereof, taken in conjunction with the accompanying drawing figures, wherein:

FIG. 1 is a front elevation view of a conduit constructed according to one embodiment of the invention for placing a source of blood in fluid communication with a target vessel;

FIGS. 13A and 13B are perspective views showing a conduit constructed according to another embodiment of the invention for placing a source of blood in communication with a target vessel, the conduit being shown in its collapsed and expanded orientations, respectively;

FIGS. 14A and 14B are perspective views showing a conduit constructed according to still another embodiment of the invention for placing a source of blood in fluid communication with a target vessel, the conduit being shown in its collapsed and expanded orientations, respectively;

FIG. 14C is an end elevation view of the conduit shown in FIG. 14A;

FIGS. 15, 16 and 17 are perspective views of conduits constructed according to other embodiments of the invention for placing a source of blood in fluid communication with a target vessel;

FIGS. 18A and 18B are, respectively, end and side elevation views of a conduit constructed according to another embodiment of the invention;

FIGS. 19A and 19B are, respectively, end and side elevation views of a conduit constructed according to yet another embodiment of the invention;

DESCRIPTION OF THE SPECIFIC EMBODIMENTS

Figure 1A:
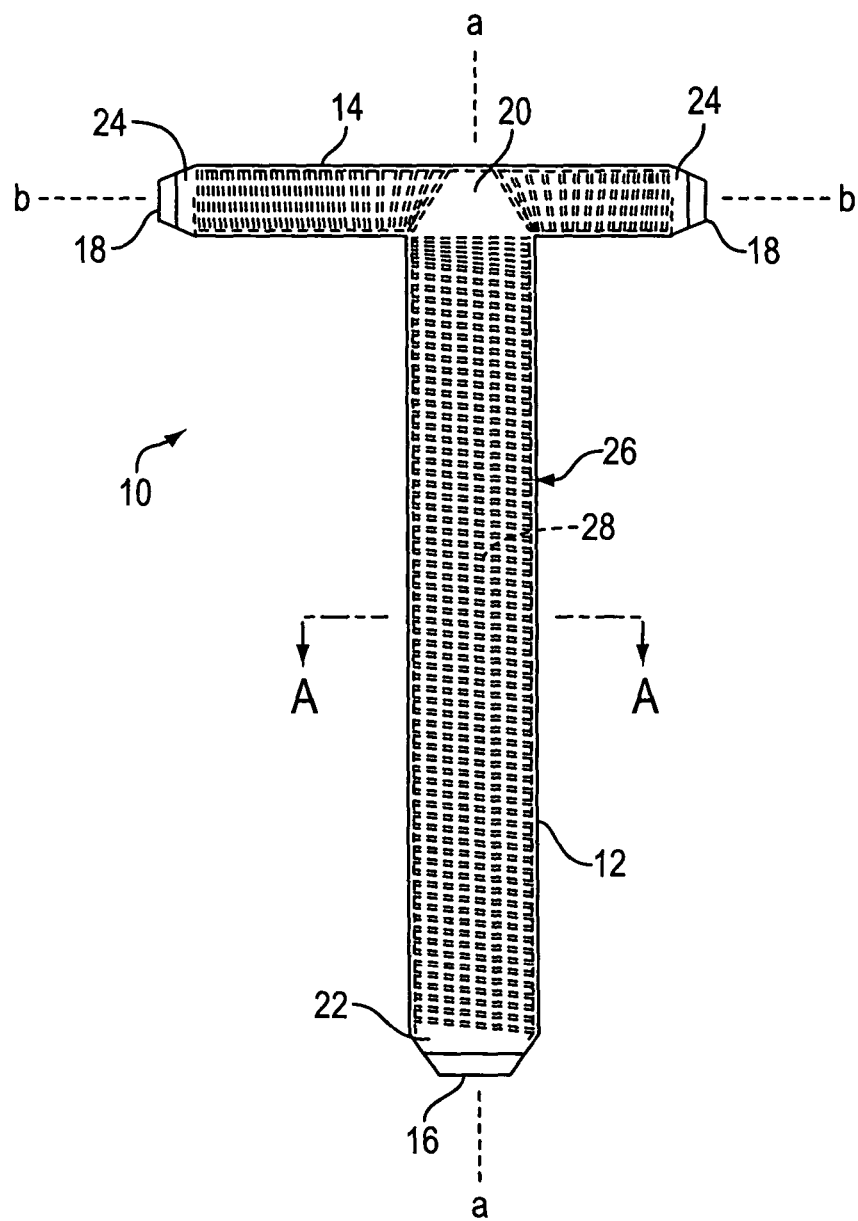
FIG. 1A is a transverse cross-sectional view taken along line A-A in FIG. 1.

The present invention provides a conduit that is placed in a patient's body to establish a flow path between a source of blood and a target vessel, as well as methods and device for deploying the conduit. In a preferred embodiment, the source of blood is a heart chamber containing oxygenated blood and the target vessel is a coronary vessel (artery or vein). It will be recognized, however, that the invention may be used to form a blood flow path between other hollow body structures. Also, as used herein, source of blood refers to any blood-containing structure, while oxygenated blood refers to blood containing some level of oxygen.

The lumen of the target vessel may be partially or completely obstructed by an occlusion and the conduit placed to form a flow path that bypasses the occlusion. Alternatively or additionally, the conduit may be used to create a supplemental blood flow path that feeds into the target vessel to augment blood flow (native or other) already present in the vessel.

The conduit of the invention may be configured in various manners. In its most preferred form, the conduit includes a first conduit portion having at least one inlet adapted to be placed in communication with a source of blood and a second portion having at least one outlet adapted to be placed in communication with the lumen of a target vessel. The first and second conduit portions may be defined by a single unitary member or several members that are attached or formed into a desired configuration. The first and second conduit portions are transverse to each other and have lumens that meet at a junction. For example, the first and second conduit portions have respective axes that extend transversely to each other to form a predetermined angle, the angle preferably being within a desired range that achieves acceptable flow characteristics.

Referring to FIGS. 1 and 1A-1C, a conduit constructed according to one preferred embodiment of the invention is indicated generally by the reference numeral 10 and includes a first conduit portion 12 and a second conduit portion 14. The first conduit portion 12 has an inlet 16 that is placed in fluid communication with a source of blood, and the second conduit portion 14 has a pair of outlets 18 that are placed in fluid communication with a target vessel. It will be appreciated that the first conduit portion 12 may have more than one inlet and the second conduit portion 14 may have one, two or more outlets. The first and second conduit portions 12, 14 have lumens in fluid communication with each other.

The illustrated conduit 10 is generally T-shaped with the first and second conduit portions 12, 14 meeting at a junction 20 such that their respective axes a, b are substantially perpendicular. It should be noted, though, that according to the invention the axes a, b of the first and second conduit portions 12, 14 could be disposed non-perpendicularly. For example, as discussed further below, rather than forming a 90° (or substantially 90°) angle, the axes a, b could extend transversely to each other to form an acute or obtuse angle (depending on whether the angle is measured from the left or right side of the axis a, as viewed in FIG. 1).

The first conduit portion 12 of the illustrated conduit 10 has a free end 22 defining the inlet 16 while the second conduit portion 14 has a pair of free ends 24 defining the outlets 18. The free ends 22, 24 may be integral extensions of their respective conduit portions or they may comprise separate members secured to the conduit. One or more of the free ends 22, 24 may have ends cut, beveled or tapered (or otherwise configured) for easier introduction into the target vessel. The end 24 of the conduit portion 14 is preferably formed of a flexible, relatively atraumatic material (e.g., as discussed below) that will not damage the endothelial cells lining the intimal surface of the target vessel, particularly during placement of the device.

The inlet 16 or outlets 18 may be located on the conduit 10 at a position(s) other than those shown in the Figures, e.g., at one or more points along the length of the conduit. Similarly, in the illustrated embodiment the first conduit portion 12 (axis a) is offset in that it does not bisect the second conduit portion 14 (axis b); this provides the second conduit portion with different size legs extending away from the first conduit portion. Configuring the target vessel portion of the conduit 10 with shorter and longer legs may be useful in introducing the conduit into the target vessel. It should nonetheless be recognized that the first conduit portion 12 may be centrally located along the axis b of the second conduit portion 14 to provide legs of equal length, or it may be offset from the axis b a greater distance than shown in FIG. 1.

Figure 1A:
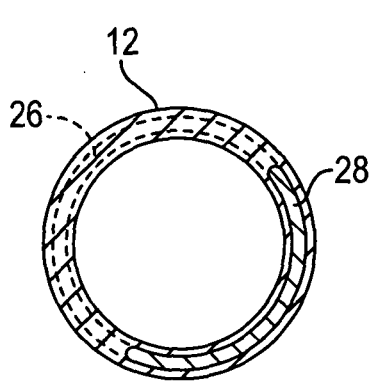
Figure 1B:
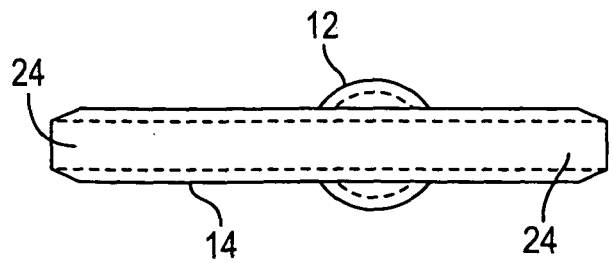
FIG. 1B is a plan view of the conduit shown in FIG. 1.

According to a preferred aspect of the invention, the conduit is provided with a reinforcing component having sufficient strength to ensure that the conduit remains open during use by preventing or reducing the likelihood of the conduit kinking or collapsing. The reinforcing component may be integrally formed with the conduit or it may comprise a separate member secured thereto. One embodiment of a reinforcing component 26 is shown in FIG. 1 (in phantom) and comprises a plurality of coils 28 which extend over the first and second conduit portions 12, 14. See FIG. 2, in which an external portion of the conduit 10 is omitted for clarity to expose the reinforcing component 26. As seen from FIG. 1A, the reinforcing component 26 is preferably encased in the body of the conduit 10 which prevents contact between blood and tissue and the reinforcing component (coils 28 in this embodiment).

In the illustrated embodiment, the spacing, as well as the size and material of construction, of the coils 28 may be used to determine the amount of structural support provided by the reinforcing component 26. As such, these variables may be selected to produce a conduit having desired characteristics. For example, one of the first and second conduit portions 12, 14 may be made more rigid or flexible than the other by varying the pitch of the coils, the thickness of the wire forming the coils, the material forming the coils, etc., on the portions. Further, the reinforcing component 26 may comprise a single coil, a first coil for the first conduit portion and a second coil for the second conduit portion, a first coil for the first conduit portion and two separate coils for the two free legs of the second conduit portion, etc. Finally, it will be noted that the reinforcing component may have a non-coiled configuration, e.g., a stent or stent-like construction, a braided structure, etc., and may comprise one or multiple members. Exemplary materials include metals or alloys, such as titanium, stainless steel or nitinol, and non-metals, such as polymers or other synthetic materials.

Figure 2:
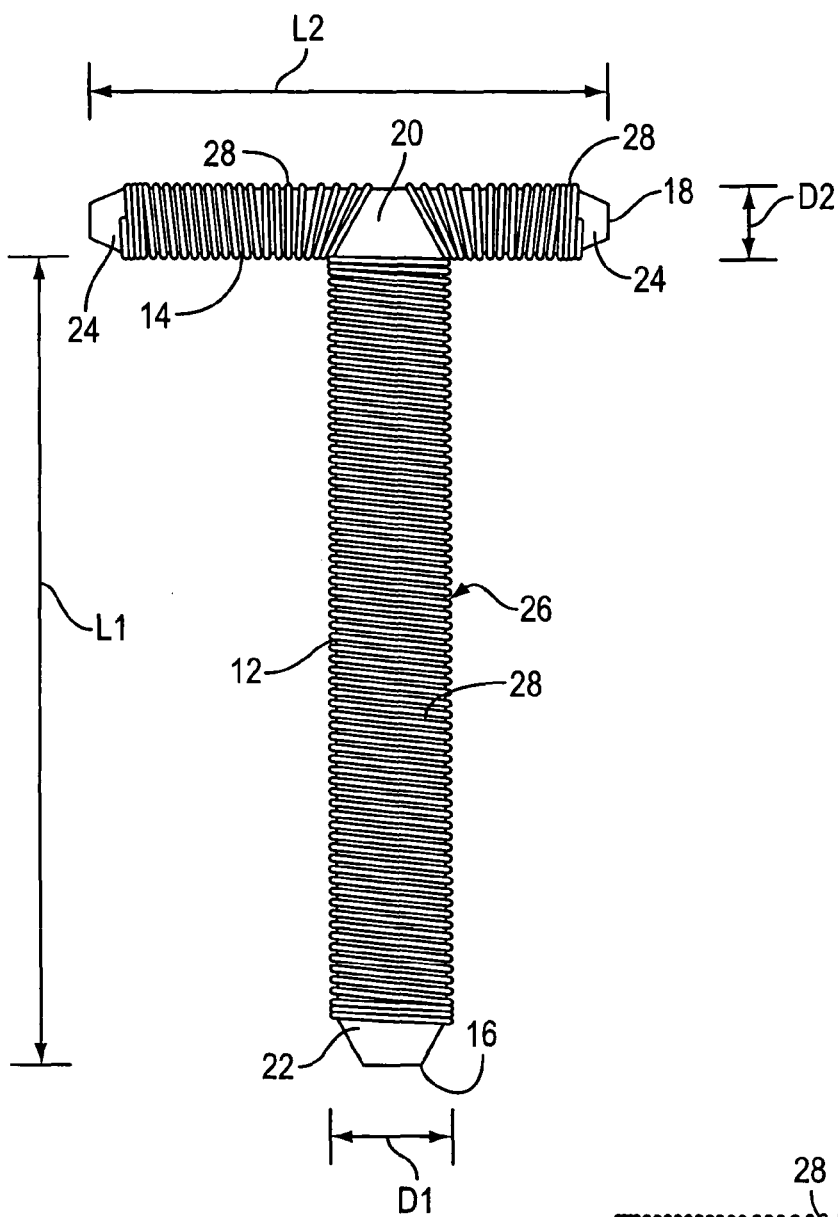
FIG. 2 is a fragmentary front elevation view of the conduit shown in FIG. 1, wherein a portion of the conduit is removed to expose a reinforcing component.
Figure 3:
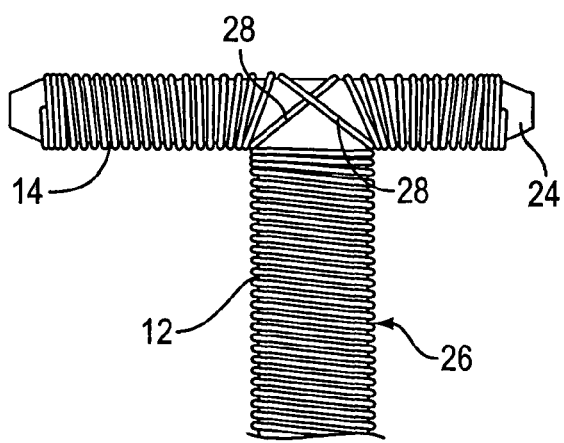
FIG. 3 is a fragmentary, front elevation view corresponding to FIG. 2 but isolating an alternative embodiment of a reinforcing component.

The second conduit portion 14 is preferably relatively flexible to allow it to yield slightly when placed in the target vessel and follow the contour of the target vessel (not shown in FIGS. 1-3). The first conduit portion 12 may be more rigid than the second conduit portion 14, particularly if the blood source is a heart chamber and the first conduit portion 12 is placed in (or secured to) myocardial tissue. In this case, the first conduit portion 12 would preferably be relatively rigid to remain open during myocardial contraction. The junction 20 of the first and second conduit portions 12, 14 is essentially unreinforced in the embodiment shown in FIGS. 1-2. The junction 20 may, however, be made selectively stiff or flexible, e.g., by disposing one or more coils 28 of the reinforcing component 26 at or adjacent the junction 20, as exemplified by the embodiment shown in FIG. 3.

It will be appreciated that the size of the conduit will vary depending on the application. Referring to FIG. 2, the first conduit portion 12 has a length L1, diameter D1 (or a different dimension if the cross-section is non-circular), while the second conduit portion 14 has a length L2 and a diameter D2. One or more of these dimensions may be changed to alter the flow characteristics that the conduit achieves in a given application, or to modify the conduit for use in different applications.

FIGS. 1-2 depict a conduit that is sized and configured for use in placing a coronary vessel in fluid communication with a heart chamber containing blood. The distal end of the first conduit portion 12 will preferably be reinforced by an additional component (not shown in FIGS. 1-2, but see element 128 in FIGS. 9-12) that is designed to remain open during systole once it has been placed in or secured to myocardial tissue. The additional reinforcing component may be positioned over a distal part of the first conduit portion 12 in telescoping fashion, or it may be secured to the end 22 of the first conduit portion 12 and extend axially away therefrom.

Figures 4, 4A:
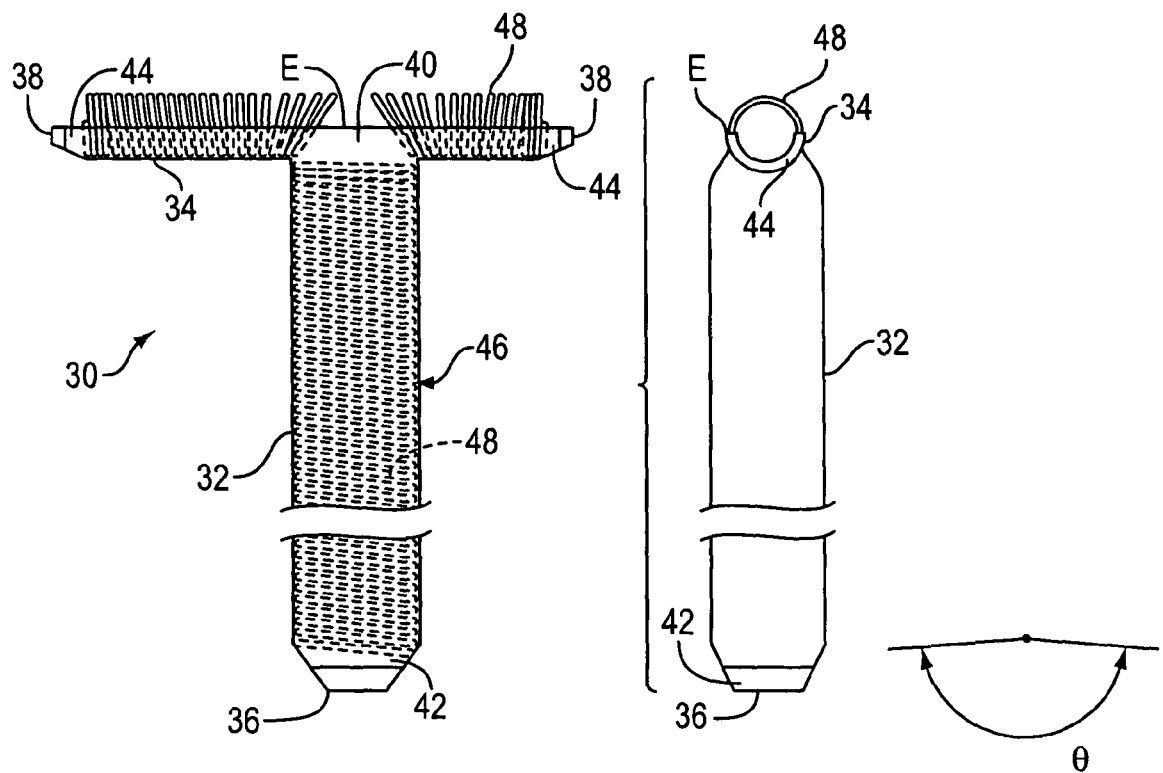
FIG. 4 is a front elevation view of a conduit constructed according to another embodiment of the invention for placing a source of blood in fluid communication with a target vessel.
FIG. 4A is a side elevation view of the conduit shown in FIG. 4.

According to another preferred embodiment of the invention, the second conduit portion comprises a tubular member that is only partially closed about its circumference, as opposed to a tubular member that is entirely closed about its circumference (as is the embodiment of FIGS. 1-3). An exemplary conduit 30 constructed according to this embodiment is shown in FIG. 4 and includes first and second conduit portions 32, 34. The conduit 30 is generally T-shaped and may be defined by a single unitary piece or several discrete pieces of material suitable for use in forming a blood flow path, and will be sized depending on the specific application, as explained above.

The first conduit portion 32 has an inlet 36 adapted to be placed in communication with a source of blood, while the second conduit portion 34 has a pair of outlets 38 for directing blood into the target vessel. The first and second conduit portions 32, 34 meet at a junction 40 having a desired amount of flexibility. For example, the first conduit portion 32 may be more rigid than the second conduit portion 34, while the second conduit portion 34 is more rigid than the junction 40. The first conduit portion has a free end 42 defining the inlet 36, and the second conduit portion has two free ends 44 defining the outlets 38. The conduit 30 is provided with a reinforcing component 46 including coils 48 that essentially correspond to the coils 28 of the reinforcing component 26 described above with respect to the embodiment of FIGS. 1-2.

Referring to FIG. 4A, the second conduit portion 34 extends through an angle θ to form approximately one half of a tubular member (θ being approximately 180° in the illustrated embodiment). This produces exposed ends or edges E on second conduit portion 34. It will be understood that the specific configuration of the conduit including the amount and location of material forming the conduit portions may be varied, for example, by varying the angle θ or modifying the profile of the edges E of the second conduit portion 34.

FIG. 4A is a side elevation view of the conduit 30 and illustrates the relative dimensions of the first and second conduit portions 32, 34, as well as the edges E of the second conduit portion that result from removing a section of the tubular element. The coils 48 of the illustrated reinforcing component 46 extend beyond the edges E of the second conduit portion 34 and support the target vessel wall around its entire (or substantially entire) circumference. In this embodiment, the coils 48 (or other structure of the reinforcing component) extend 360° and, along with the second conduit portion 34, define a complete tubular element with openings between adjacent coils. The conduit of the invention may instead have a reinforcing component that supports less than the entire circumference of the target vessel wall.

Figures 5, 5A:
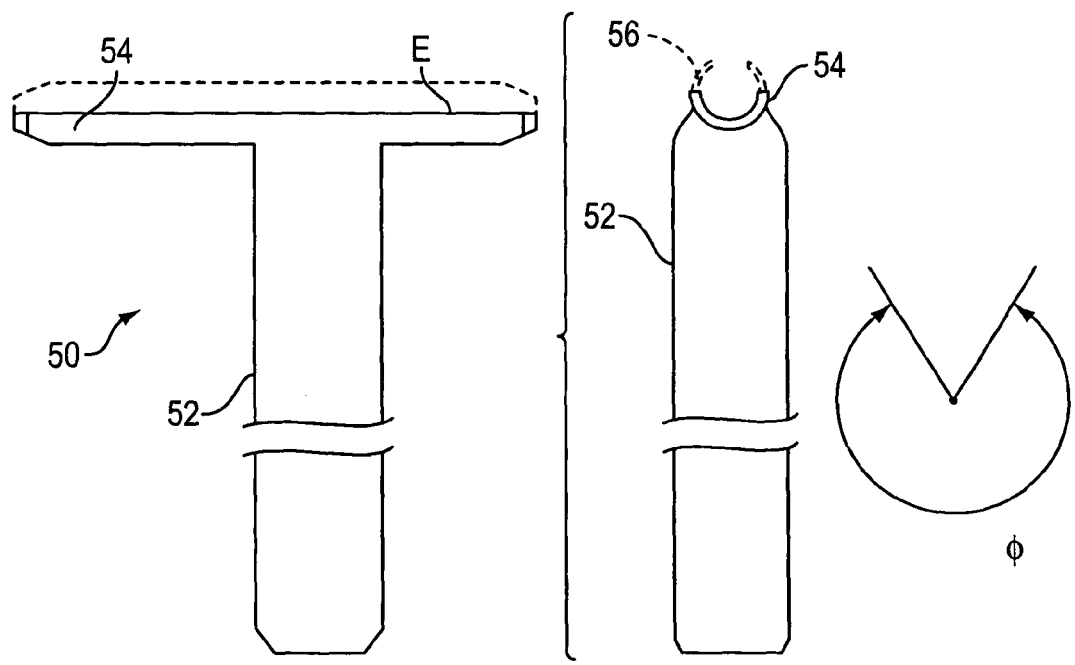
FIG. 5 is a front elevation view of a conduit constructed according to another embodiment of the invention for placing a source of blood in fluid communication with a target vessel.
FIG. 5A is a side elevation view of the conduit shown in FIG. 5.

FIGS. 5 and 5A show a conduit 50 that comprises first and second conduit portions 52, 54 and has a construction that is essentially the same as that of the conduit 30. The conduit 50, however, is not provided with a reinforcing component. As shown in solid lines in FIG. 5A, the second conduit portion 54 is the same as the second conduit portion 34 of the conduit 30 shown in FIGS. 4 and 4A in that each portion extends through an angle θ to define approximately one half of a tubular member. It should be recognized that the second conduit portion may extend in an angular or circumferential direction more or less than that shown in FIGS. 4A and 5A. For example, FIG. 5A shows (in phantom) a second conduit portion 56 extending over an angle φ that is greater than the angle θ, the angle φ being approximately 300°, which is only one example of the many possible conduit configurations. As an example, for use in treating coronary vessels, which typically will have a diameter in the range of 1 to 4 mm, the angles θ and φ are preferably in a range of from about 90° to 300°, more preferably 90° to 240°, and most preferably 180° to 240°.

One benefit of the embodiment shown in FIGS. 4-4A and 5-5A is that a relatively small amount of conduit material must be accommodated in the target vessel lumen, thereby providing more space to deliver blood. Another benefit is that when the second conduit portion is positioned within the lumen of a target vessel, a portion of the inner (posterior) wall of the target vessel remains relatively unobstructed by the conduit. As a result, in the case of a coronary artery as the target vessel, for example, any septal perforators that lie beneath the conduit remain completely (or substantially) unobstructed to feed blood to the myocardial tissue. Further, any diagonal branches of the vessel that emanate from an area at (or near) the location of the second conduit portion also would remain unblocked by the conduit. Finally, the partial tubular conduit is flexible and may be used to treat different size vessels because the edges E of the second conduit portion may be positioned at various locations along a vessel wall.

Moreover, this embodiment of the invention is particularly useful in treating the coronary arteries of patient's suffering from arteriosclerosis. That is, the inner or posterior wall of a diseased coronary artery will typically be covered with stenosis or plaque; as a result, contacting this area with a device may lead to various problems, such as dislodging stenotic material or damaging any healthy tissue that still exists. This embodiment provides conduits that are positioned within the lumen of the artery without contacting much of the diseased inner artery wall.

This is in contrast to a conduit having a portion that substantially or completely covers the luminal surface of the wall of the target vessel, thereby covering the inner vessel wall and restricting or blocking flow between the vessel and any diagonal branches or septal perforators. This aspect of the invention is described further in connection with the Figures below which illustrate exemplary methods of using conduits constructed according to the invention. Nonetheless, the conduit of the invention may be positioned transmurally if desired.

The illustrated conduits 10, 30, 50, comprises a single, unitary piece of material (excepting the reinforcing component) that has been formed into a desired configuration. This construction may be preferable to minimize the risk of material separation or other adverse effects to the structural integrity of the conduit. Nonetheless, the conduit of the invention may comprise several pieces of material secured together. Similarly, the reinforcing component may comprise a structural member integrally formed with or coupled to the conduit, or a reinforcing material added to or impregnated in the material forming the conduit.

Figure 6:
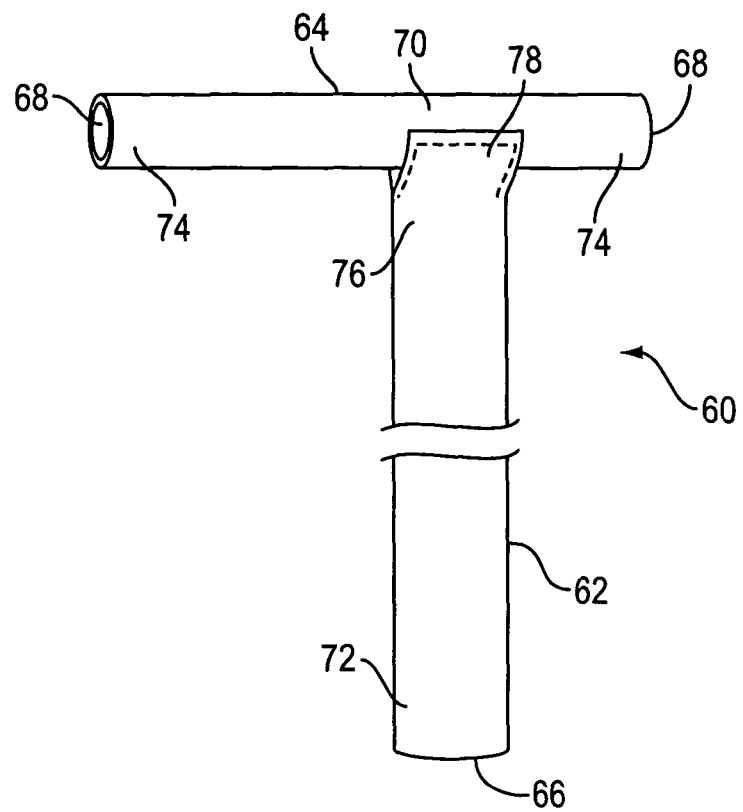
FIGS. 6, 7 and 8 are perspective views of conduits constructed according to other embodiments of the invention for placing a source of blood in fluid communication with a target vessel.

An exemplary conduit formed of discrete pieces of material is designated by reference numeral 60 in FIG. 6 and includes a first conduit portion 62 and a second conduit portion 64 which correspond, respectively, to the first and second conduit portions of the previous embodiments. As such, the first conduit portion 62 has at least one inlet 66 while the second conduit portion 64 has at least one outlet 68. The conduit portions 62, 64 are joined at a junction 70 by suitable means, e.g., adhesives, thermal bonding, mechanical attachment, etc. The first conduit portion 62 has a free end 72 defining the inlet 66 and the second conduit portion 64 has two free ends 74 defining two outlets 68. The illustrated conduit 60 does not include a reinforcing component coupled to or formed with the body of the conduit; however, the above-described reinforcing components may be used, or the conduit 60 may be partially or completely coated (or otherwise treated) with a layer of reinforcing material that prevents collapsing or kinking of the conduit.

The first conduit portion 62 of this embodiment has an opposite end 76 which is bifurcated into two flaps 78 each of which is secured to the conduit portion 64 by any of the aforementioned means. The edges of the flaps 78 may be tapered or feathered (as shown) to make a smooth transition with the exterior of the second conduit portion 64, thereby minimizing the amount of material to be introduced into the lumen of the target vessel. It also may be preferable to minimize the wall thickness of the material used to further reduce the amount of material that must be accommodated when the second conduit portion is placed in the target vessel lumen, without sacrificing preferential blood flow characteristics or the structural integrity of the conduit.

Figure 7:
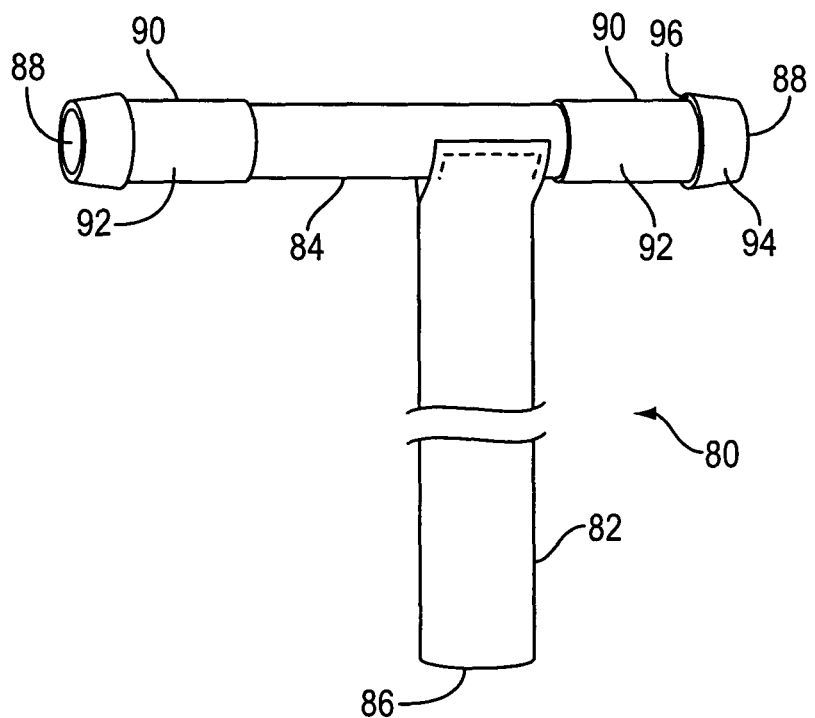

FIG. 7 shows a conduit 80 constructed according to another embodiment of the invention. The conduit 80 includes first and second conduit portions 82, 84 secured together and having, respectively, an inlet 86 and a pair of outlets 88. The second conduit portion 84 has a pair of free ends 90 that define the outlets 88. The free ends 90 of the second conduit portion 84 are provided with reinforcing components 92 which engage and support the wall of the target vessel adjacent the outlets 88.

Each reinforcing component 92 preferably has a beveled, slightly enlarged end 94, e.g., as a barb, for easy introduction into the target vessel lumen, although only one of the components 92 may be beveled and/or enlarged. Each component 92 also has a step 96 for receiving a suture (not shown) or other fastening means that may be used to enhance attachment between the second conduit portion 84 and the target vessel. It will be appreciated that the specific construction of the reinforcing components 92 and the conduit 80 may be different from that shown, e.g., grooves, slots, resilient collars, roughened surfaces, etc.

Figure 8:
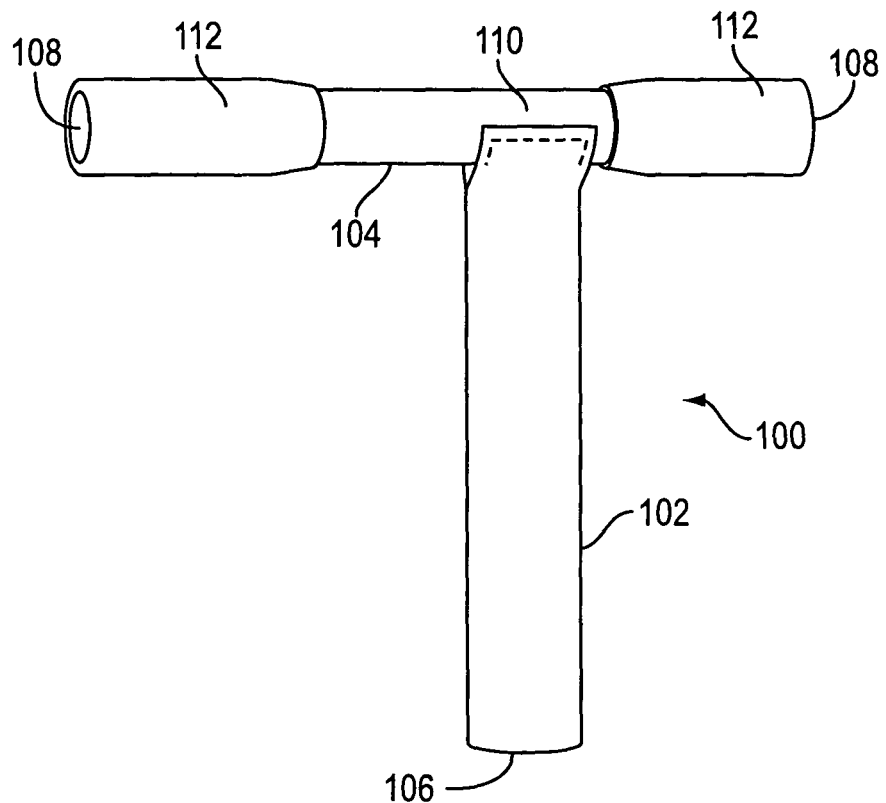
Figure 8A:
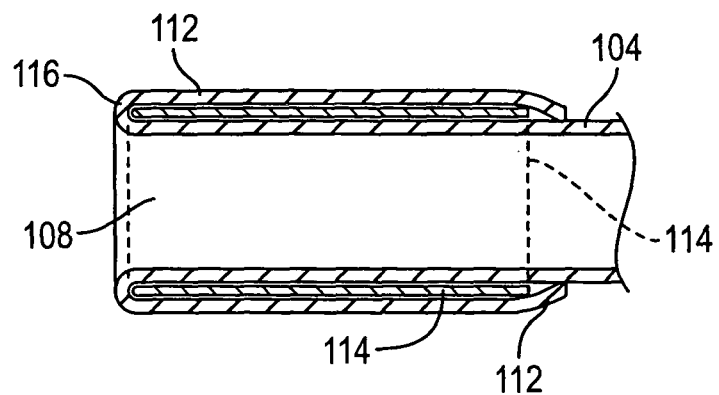
FIG. 8A is a longitudinal cross-sectional view taken through one end of the conduit shown in FIG. 8.

FIGS. 8 and 8A illustrate a conduit 100 constructed according to another embodiment of the invention. The conduit 100 is similar to the conduit 80 and includes first and second conduit portions 102, 104 defining, respectively, an inlet 106 and a pair of outlets 108. The first conduit portion 102 has an end secured to the second conduit portion 104 at a junction 110 by any of the means described herein. The second conduit portion 104 has a pair of ends 112 defining the outlets 108, each end 112 being provided with a reinforcing component 114 to engage and support the wall of the target vessel adjacent the outlets 108 (FIG. 8A).

The conduit 100 is constructed such that the reinforcing components 114 do not come into direct contact with the luminal surface of the target vessel wall. As shown in FIG. 8A, the reinforcing components 114 are disposed on the exterior of the second conduit portion 104; however, the ends 112 of the second conduit portion 104 are everted at 116 so as to capture the reinforcing components 114. This ensures that the material of the second conduit portion 104 (which has beneficial blood interface characteristics) contacts the blood flowing through the target vessel, rather than the reinforcing components 114. It will be understood that while the illustrated reinforcing components 114 are sleeves that extend around the circumference of the ends 112 of the second conduit portion 104, they could have a different construction, e.g., coil members, and they could extend around a portion of the ends of the conduit portion, e.g., by placing a plurality of discrete members around some or all of the second conduit portion 104.

Figure 9:
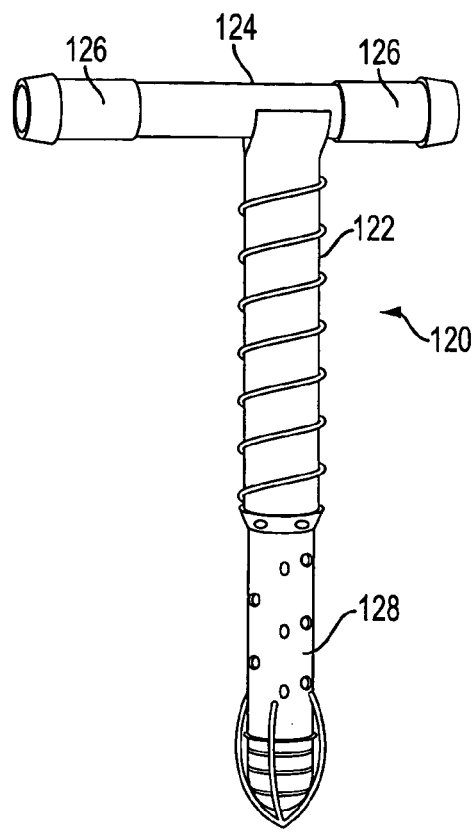
FIGS. 9, 10, 11 and 12 are perspective views of conduits constructed according to other embodiments of the invention for placing a source of blood in fluid communication with a target vessel.

FIGS. 9-12 illustrate several conduits constructed according to further alternative embodiments of the invention. FIG. 9 shows a conduit 120 including first and second conduit portions 122, 124 for communicating, respectively, with a source of blood and a target vessel. The conduit 120 has basically the same construction as the conduit 100 described above, including reinforcing components 126 at the ends of the second conduit portion 124. The conduit 120 is configured for use in placing a coronary vessel in fluid communication with a heart chamber containing blood. To that end, the conduit 120 is provided with a device 128 which is positioned in the myocardium (not shown in FIG. 9) and directs blood to the second conduit portion 124 and the target vessel.

The device 128 is preferably capable of withstanding myocardial contraction during systole so that the conduit 120 remains open during use. The construction and use of the device 128 may be in accordance with the teachings of copending, commonly-owned application Ser. No. 09/304,140, filed on May 3, 1999, and entitled "Methods and Devices for Placing a Conduit in Fluid Communication with a Target Vessel," the entire subject matter of which application is incorporated herein by reference. It will be recognized that the first conduit portion could be secured to tissue by other means, for example, suture, fasteners, clamps, clips, etc.

Figure 10:
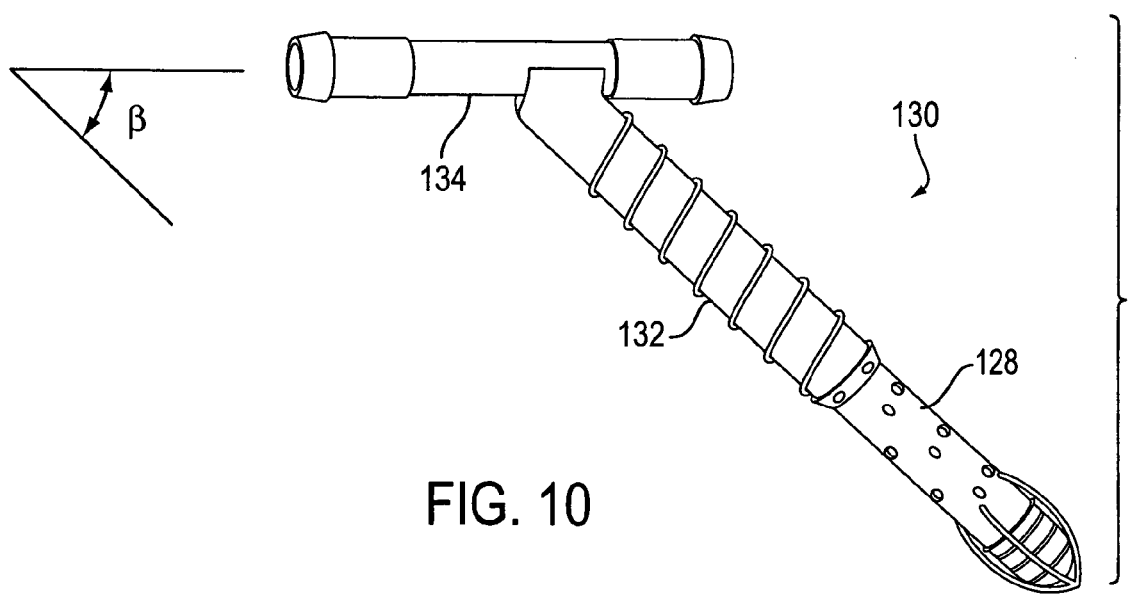

FIG. 10 shows a conduit 130 including first and second conduit portions 132, 134, which, as in the previous embodiment, respectively communicate with a heart chamber containing blood and a coronary vessel. The conduit 130 includes reinforcing components 136 on the ends of the second conduit portion 134, as well as the device 128 described above in connection with the previous embodiment. The conduit 130, rather than being generally T-shaped, has a different configuration due to the longitudinal axes (not shown) of the first and second conduit portions 132, 134 being arranged in a non-perpendicular fashion.

Specifically, the first conduit portion 132 extends away from the second conduit portion 134 at an angle θ which, in the illustrated embodiment, is approximately 45°. It may be desirable to angle the first and second conduit portions with respect to each other to achieve different flow characteristics, the particular configuration shown in FIG. 10 being exemplary only. The angle θ is preferably within a range of from about 10° to about 90°, e.g., 15°, 30°, 45°, 60°, etc., and most preferably 45°.

Figure 11:
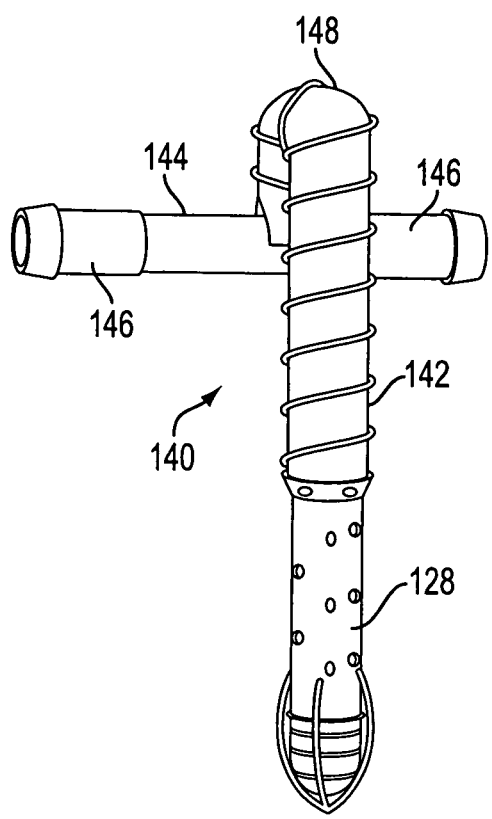

FIG. 11 shows a conduit 140 constructed according to yet another embodiment of the invention, the conduit 140 including first and second conduit portions 142, 144. As in the previous embodiment, the first and second conduit portions 142, 144 are respectively placed in communication with a heart chamber containing blood and a coronary vessel. Also as in the previous embodiment, the conduit 140 includes reinforcing components 146 on the ends of the second conduit portion 144, and the device 128 for coupling the conduit to tissue. The conduit 140, and in particular the first conduit portion 142, is constructed with a preformed curvature 148 to aid in locating the second conduit portion 144 in a coronary vessel and the second conduit portion 142 in the myocardium. The curvature may be imparted to the conduit 140 in any suitable manner, for example, by forming the conduit on a curved mandrel.

Figure 12:
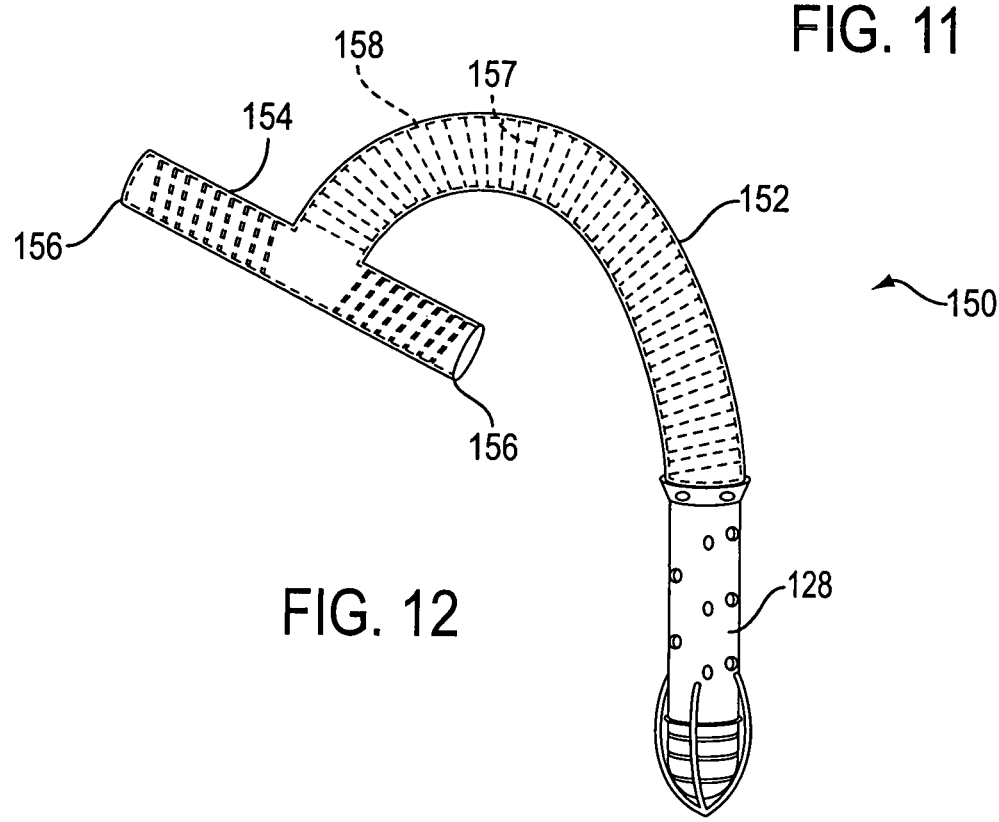

FIG. 12 shows a conduit 150 constructed according to still another embodiment of the invention. The conduit 150 includes first and second conduit portions 152, 154, and a device 128 for coupling the conduit to tissue. The second conduit portion 154 has one or more beveled ends 156 (but not the reinforcing components included in the conduits 120, 130 or 140). The conduit 150 instead has a reinforcing component 157 having a coiled construction that is the same as (or similar to) the reinforcing component 26 described in connection with FIGS. 1-2. The first conduit portion 152 has a preformed curvature 158 to aid in locating the second conduit portion 154 in a coronary vessel. The curvature 158, however, is less severe than the curvature 148 of the conduit 140. It will be appreciated that the conduits 140, 150 of FIGS. 11 and 12 are only two examples of the many possible conduit shapes, as various degrees of curvature may be imparted to the first conduit portion.

FIGS. 13A-13B show a conduit 160 constructed according to still another embodiment of the invention. The conduit 160 has first and second conduit portions 162, 164 for purposes explained above. The second conduit portion 164 in this embodiment is movable between collapsed (FIG. 13A) and expanded (FIG. 13B) orientations to aid in introducing the portion 164 into the target vessel. The second conduit portion 164 has a pair of free ends 166 provided with resilient elements 168 that permit the ends 166 to move longitudinally toward and away from the first conduit portion 162 while remaining generally aligned with the longitudinal axis of the portion 164. The illustrated elements 168 are coil springs; however, alternative elements could be used, for example, self-expanding or balloon-expandable stents. The second conduit portion 164 may be collapsed to the position shown in FIG. 13A for quick and easy introduction into the target vessel lumen and, once disposed therein, expanded to the position shown in FIG. 13B.

FIGS. 14A-14C show a conduit 170 which is constructed according to another embodiment of the invention and includes first and second conduit portions 172, 174. As in the embodiment of FIGS. 13A-13B, the second conduit portion 174 is movable between collapsed (FIG. 14A) and expanded (FIG. 14B) orientations to aid in introducing the conduit portion 174 into the target vessel. The second conduit portion 174 is constructed so that it may be collapsed in a radial direction, for example, by being folded as indicated at 176 in FIG. 14C, which reduces the profile of the portion 174 for easier introduction into the target vessel lumen. The second conduit portion may be self-expanding or it may be expanded by force applied, for example, by a balloon. While the illustrated second conduit portion 174 is not provided with resilient elements as in the previous embodiment, they could be included to aid in collapsing and expanding the portion 174. The second conduit portion 174 is placed in the target vessel and expanded to the position shown in FIG. 13B such that the ends 178 of the portion 174 engage the vessel wall.

It should be recognized that the embodiments of FIGS. 13A-13B and 14A-14C are illustrative in that a conduit constructed according to the invention may be collapsible in additional or alternative fashions. For example, with respect to the embodiment of FIGS. 13A-13B, the second conduit portion 164 could be collapsed axially by folding or rolling each leg toward the first conduit portion 162. Similarly, with respect to the embodiment of FIGS. 14A-14C, the second conduit portion 174 could be collapsed radially by folding or rolling the portion in a spiral fashion. Further, the second conduit portion could be collapsible axially or longitudinally, as shown in FIGS. 13A-13B, as well as collapsible radially, as shown in FIGS. 14A-14B, by utilizing a material that expands both radially and longitudinally. For example, the material disclosed in U.S. Pat. No. 4,955,899 may be used, the disclosure of which is incorporated herein by reference.

FIGS. 15-17 show conduits constructed according to other embodiments of the invention. The conduit 180 of FIG. 15 has a first conduit portion 182 and a reduced size second conduit portion 184. The length of the second conduit portion 184 is between one and two times the diameter of the first conduit portion 182. FIG. 16 shows a conduit 186 including a first conduit portion 188 and a second conduit portion 190, the first conduit portion 188 having a restricted section 192 adjacent the conduit portion 190. FIG. 17 shows a conduit 194 that is generally L-shaped and includes first and second conduit portions 196, 198. The first and second conduit portions 196, 198 meet at a junction such that the portion 198 slightly flares away from the portion 196, thereby engaging and sealing against the edges of the incision in the target vessel wall (not shown) to prevent blood leaking out of the lumen.

FIGS. 18A-18B and 19A-19B shows conduits constructed according to other embodiments of the invention. The conduit 200 (FIGS. 18A and 18B) includes first and second conduit portions 202, 204, with a device 206 coupled to the portion 204 for communicating with the heart chamber. The first conduit portion 202 has an inlet 208 and includes multiple bends 210a, 210b which serve to align the second conduit portion 204 with the axis of the target vessel. The second conduit portion 204 includes one outlet 212, which gives the conduit an L-shaped configuration, received in the vessel to deliver blood from the chamber into the vessel lumen.

The conduit 220 (FIGS. 19A and 19B) includes first and second conduit portions 222, 224 and a device 206 for communicating with the heart chamber. The first conduit portion 222 has an inlet 226, while the second conduit portion 204 has a pair of outlets 228, giving the conduit 220 a T-shaped configuration. The conduit 220 includes multiple bends 230a, 230b which are similar to bends 210a, 210b (described above) and serve to align the second conduit portion 224, and in particular the outlets 228, with respect to lumen of the target vessel. The bends 210a, 210b and 230a, 230b may be imparted to their respective conduit in various manners. For example, a mandrel having a shape and size complementary to that of the conduit may be dipped in a suitable biocompatible material, e.g., silicone, and then heated or subjected to other conditions to cause the material to set and form the desired conduit configuration. Two or more bends are preferably imparted to the conduit so as to lie in two transverse planes, for example, substantially perpendicular planes as in the embodiments of FIGS. 18A-18B and 19A-19B. It should be recognized, though, that the particular angular orientation used, as well as the overall configuration of the conduit, may be varied depending on the specific application and user preference.

The multiple bends in the embodiments of FIGS. 18A-18B and 19A-19B allow the conduit communicating with the heart chamber to be placed through the myocardium at a location that is spaced from the coronary vessel. This is contrast to placing a conduit transmurally through the myocardium between the inner or posterior wall of the target vessel and the heart chamber so that blood flows directly through the heart wall into the vessel lumen. This provides flexibility in that the portion of the conduit communicating with the heart chamber may be placed through the myocardium at different locations while still accessing the target vessel in a desired manner with another portion of the conduit, a particularly useful feature in situations presenting limited access to the heart or target vessels.

The conduits of the invention may be formed of any material suitable for use in a blood-contacting application, for example, synthetic vascular graft materials such as expanded polytetrafluoroethylene (PTFE) and polyethylene terephthalate (Dacron). Other suitable synthetic materials include polyurethanes, such as Tecoflex, polycarbonate polyurethane—PCPU, such as Biospan (Corethane), and silicone, such as MED-4850, MED-6640, and MED-gumstock, all commercially available from NuSil Technology of Carpinteria, Calif. The conduit may also be formed of metal or a metallic alloy such as titanium, stainless steel, and nickel titanium. Finally, it should be noted that the conduit could comprise a tissue graft, for instance, a saphenous vein graft harvested from the patient, an allograft or a xenograft. It will also be appreciated that the conduit may comprise any of the aforementioned materials alone or in combination. Also, the conduits may be provided with means for detecting its position, e.g., radiopaque markers, during or after placement of the conduit in the target vessel, thereby allowing the user to confirm the position of and blood flow through the conduit.

The reinforcing component of the invention is preferably formed of any biocompatible material that will provide the conduit with a desired amount of structural support. Examples of suitable materials include Dacron, or polyethylene terephthalate (PET), Nylon, titanium, stainless steel, nickel titanium, etc. The reinforcing component could take various forms, including the coiled structure shown in FIGS. 1 and 2, a braided structure, a stent or stent-like structure, knitted fabric, woven mesh, and a tubular (or semi-tubular) element.

The conduit may also be constructed to minimize or prevent kinking or collapsing without incorporating a reinforcing component, for example, by coating or impregnating the conduit with a material that provides a desired amount of structural rigidity, such as silicone, polyurethane, PTFE, or another polymer, which would not adversely affect the flexibility or structural integrity of the conduit. For example, a coating could be placed on the interior of the conduit to maintain the conduit-blood interface while providing a strain relief-type structure to minimize or prevent kinking. The coating could, however, also be located on the exterior of the conduit (in addition to or instead of the exterior). The conduit may be provided with additional coatings selected to provide particular qualities, for example, antithrombogenic, antimicrobial lubricious, etc., coatings.

The conduit of the invention is preferably relatively flexible so that it may bend or flex during use, although it may be stiff or substantially rigid if desired. The degree of flexibility (or rigidity) imparted to the conduit may vary depending on the particular application and user preference. As an example, in a coronary application the conduit portion placed in the coronary vessel may comprise a material having a Shore hardness in the range of from about 80A to about 55D, this range being preferable because it provides sufficient structural integrity while allowing some flexibility for easier deployment.

In addition to, or in lieu of, providing the conduit with a strain relief element to counteract collapse or kinking, the conduit (or portion of the conduit) may be specifically formed to prevent kinking, for instance, by imparting a preformed bend to one or more desired areas of the conduit, as exemplified by the conduits 140, 150 shown in FIGS. 11-12. The conduit of the invention may be straight, tapered, curved, stepped, or otherwise configured over or all or a part of its length. Also, the conduit may be formed with a curved, malleable or bendable portion, or an articulated portion that may be controlled or steered by known mechanisms used to steer catheters or guide wires.

Turning to FIGS. 20A-30E, exemplary embodiments of methods for placing a conduit in fluid communication with a target vessel and a source of blood according to the invention will be described. These embodiments show a conduit being used to place a coronary vessel, such as a coronary artery or vein, in fluid communication with a heart chamber, such as the left ventricle. It will be understood, however, that these particular applications are set forth for explanatory purposes and are not intended to restrict or limit application of the invention to other body structures.

In the illustrated and preferred embodiments, the conduit is secured to the target vessel by a substantially suture-free attachment; thus, the attachment is not a conventional hand-sewn anastomosis created by suturing the members together. Although some suture may be used, the conduit is preferably coupled to the target vessel by means other than a typical, hand-sewn sutured connection. It will nonetheless be appreciated that the invention may be practiced using suture to secure (partially or completely) the conduit to the target vessel.

Figure 20A:
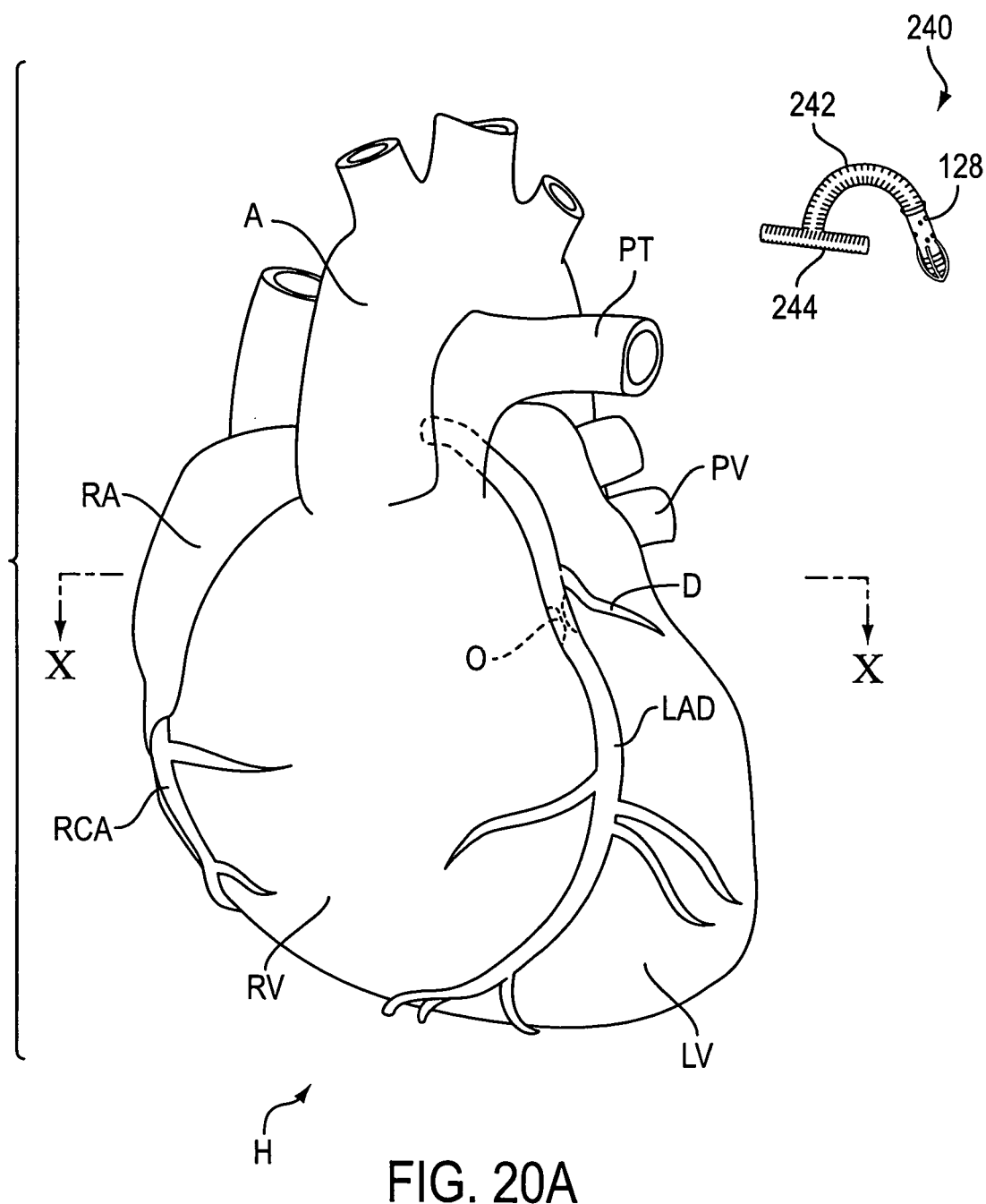
FIG. 20A is a perspective anterior view of a heart and a conduit constructed according to one embodiment of the invention.

FIG. 20A is an anterior view of a heart H showing the left ventricle LV, right ventricle RV, right atrium RA, aorta A, pulmonary trunk PT and pulmonary veins PV. The left coronary artery, including its left anterior descending branch LAD, is visible in this view, as is the right coronary artery RCA. Also shown is a diagonal branch D of the LAD. The coronary arteries run along the myocardium and deliver oxygenated blood to the myocardial tissue. An occlusion or stenosis O partially (or completely) obstructs the lumen of the LAD, which results in inadequate or no blood flow to the myocardial tissue fed by the portion of the LAD that is downstream of the occlusion O. It will be appreciated that the occlusion O could be located in another coronary artery, or in a different location in the LAD, for example, proximal rather than distal to the diagonal branch D.

FIG. 20A shows a conduit 240 constructed according to the invention positioned adjacent the heart H. The conduit 240 includes first and second conduit portions 242, 244 adapted to be placed in communication with a heart chamber and a target vessel, respectively. The conduit 240 includes a device 128 for establishing communication with a heart chamber while securing the conduit in the desired position, as well as a reinforcing component for supporting the walls of the conduit.

Figure 20B:
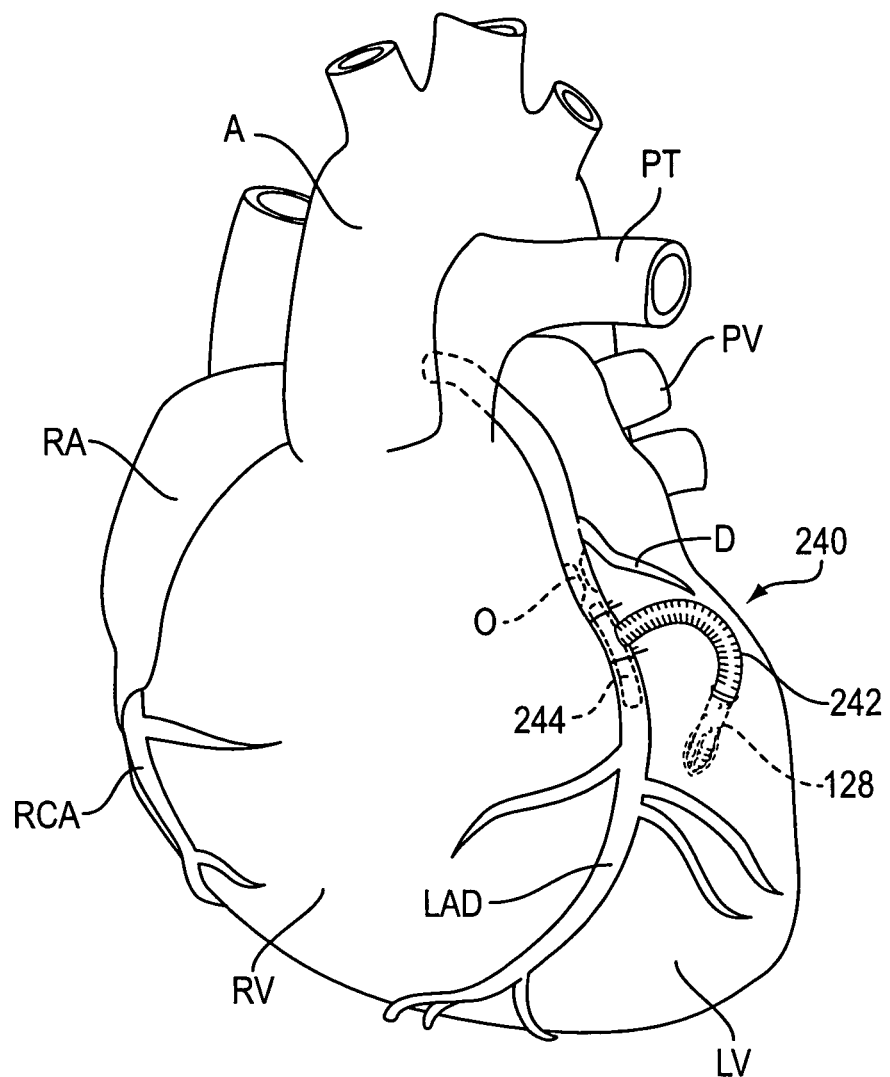
FIG. 20B is a perspective view of the heart shown in FIG. 20A after the conduit has been deployed to carry out a coronary bypass procedure.

FIG. 20B depicts the heart H shown in FIG. 20A after the second portion of the conduit 240 has been deployed in the target vessel. The device 128 is inserted into the tissue of the myocardium, either before or after deployment in the target vessel, so as to be in fluid communication with a heart chamber containing oxygenated blood (the left ventricle LV in the illustrated embodiment). The first conduit portion 242 extends from the device 128 to the coronary vessel being treated (the LAD in the illustrated embodiment). The second conduit portion 244 is disposed in the LAD at a location distal to the occlusion O so as to contact and seal against the luminal surface of the vessel wall. As a result, blood flows from the left ventricle LV into the conduit 240 and the lumen of the LAD to perfuse myocardial tissue distal to the occlusion O, which tissue had been deprived of oxygenated blood due to the occlusion.

Figure 20C:
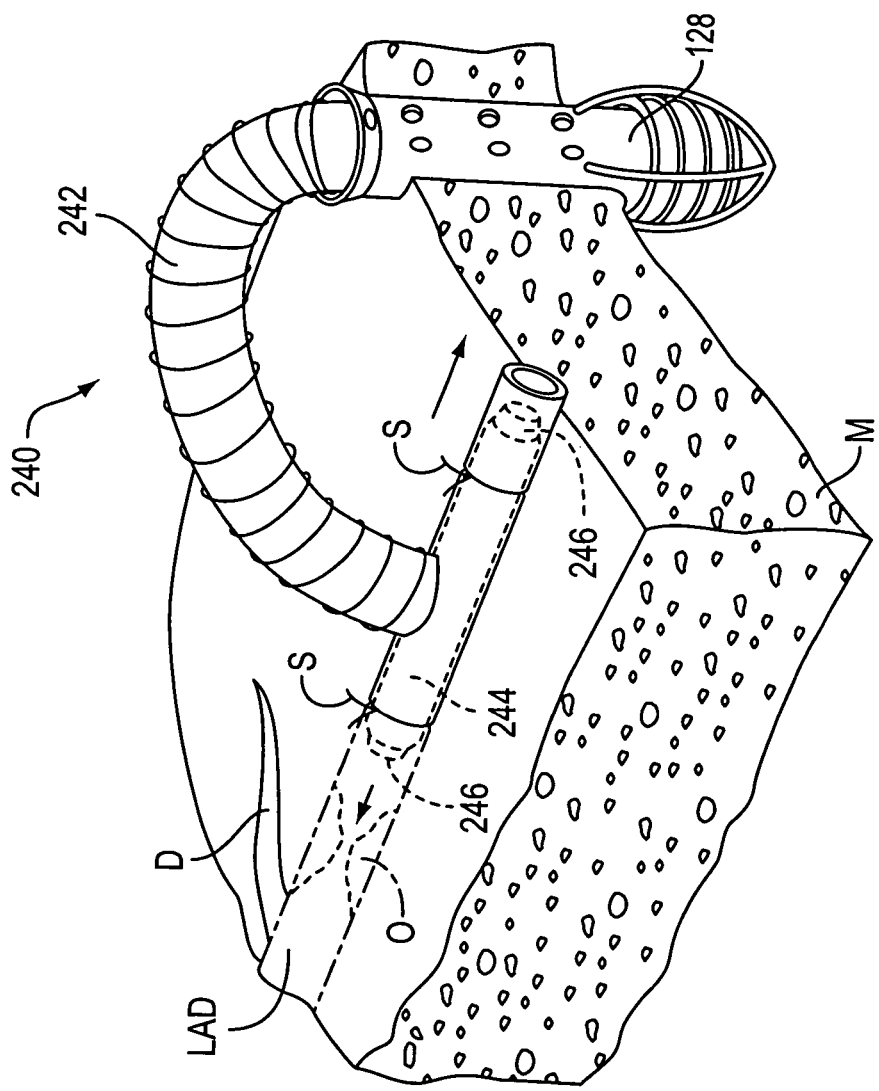
FIG. 20C is an enlarged sectional view of a portion of the heart shown in FIG. 20B.

FIG. 20C is an enlarged view of a portion of the heart H shown in FIG. 20B. The device 128 is shown positioned in the myocardium M so as to communicate with the left ventricle LV (the reinforcing component being omitted in this view). The device 128 is preferably sized so that when positioned it extends completely through the myocardium M and projects slightly into the left ventricle LV and slightly beyond the exterior of the myocardium. Alternatively, the device 128 could terminate within the myocardium with a distal segment of the first conduit portion 242 extending into the myocardium. As another alternative, the device 128 could be omitted and the first conduit portion 242 positioned in the myocardium so as to extend into the left ventricle, the portion 242 being constructed to withstand myocardial contraction during systole without collapsing.

In any case, it may be desirable to first measure the thickness of the myocardium, either approximately or precisely, at the area that will receive the device 128 (or the distal segment of the first conduit portion 242). The device 128 may then be placed with its ends properly positioned with respect to the left ventricle and the exterior of the myocardium. Any suitable means for determining the thickness of the myocardium may be used prior to placing the conduit 240. For example, an instrument having markings may be inserted through the myocardium to gauge the myocardial thickness. The instrument, for example, a probe, may have a member on its distal end that is engaged with the endocardium, thereby allowing the user to read the markings disposed adjacent the exterior of the heart. Alternatively, an instrument having a flashback lumen may be used so that entry into the heart chamber is indicated or verified by a blood flash, the instrument having markings that may be read to determine myocardial thickness or verify entry into the source of blood (or the target vessel). Other means for determining myocardial thickness include transesophageal echocardiography (TEE), magnetic resonance imaging, CT scanning and electronic probes.

The second conduit portion 244 includes two outlets 246 and may be placed into the lumen of the LAD through an incision I and, if desired, secured in place by suture S. It should be noted that if the occlusion O is not complete (or if blood from collateral vessels feeds into the LAD proximal to the conduit 240), the outlet 246 that is proximal to the first conduit portion 242 (the outlet to the left in FIG. 20C) also acts as an inlet as blood enters this outlet and flows distally. During diastole, this blood may be drawn from the vessel into the left ventricle due to the relatively low ventricular pressure, as discussed further below.

The second conduit portion 244 will typically be placed in the target vessel distal to the occlusion by a distance that permits easier introduction into the lumen, as opposed to entering a diseased or stenosed section of the vessel. This results in a space located between the occlusion O and the conduit outlet 246 that is disposed nearest the occlusion (the outlet to the left in FIG. 20C). Thus, if the conduit does not provide blood flow toward the occlusion O, this space, and more particularly the myocardial tissue fed by this section of the LAD, may become ischemic, particularly if the occlusion totally blocks any native flow through the vessel from an upstream source.

Accordingly, the preferred embodiments of the invention utilize conduits that are configured to deliver blood into the target vessel in multiple directions to fully revascularize the myocardial tissue perfused by the vessel. As shown in FIG. 20C, blood flows into the second conduit portion 244 and exits the outlets 246 in more than one direction, as indicated by the arrows. In the illustrated embodiment the directions are along a common axis and opposite each other, but it will be recognized that the embodiment of FIGS. 20A-20C is only one possible configuration that will result in blood flowing into the target vessel in multiple directions. As such, the invention encompasses delivering blood into the target vessel in multiple directions that are not opposite each other. For example, rather than being T-shaped, an L-shaped conduit such as conduit 294 shown in FIG. 17 may be used. It should be recognized that the invention encompasses conduits that are not T or L-shaped but are still configured to achieve flow in more than one direction within the target vessel.

The multiple outlets in the preferred conduit permit subsequent access to the conduit (i.e., post procedure) by delivering a guidewire or catheter percutaneously through the patient's vascular system. For example, the catheter may be delivered into the coronary vessel and moved past the occlusion, if possible, and then used to guide a device to the conduit location, e.g., a plaque ablation or removal device.

In an application utilizing the left ventricle as the blood source, such as that depicted in FIGS. 20A-20C, the direction and volume of the blood flow in the coronary vessel will vary during the systolic and diastolic phases of the heart cycle. More particularly, during systole the pressure in the left ventricle is at its maximum, approximately 120 mm Hg, which forces blood into the conduit 240. The blood flows from the first conduit portion 242 into the second conduit portion 244 and passes through the outlets 246 into the LAD. The high pressure in the left ventricle drives the blood in multiple directions to perfuse the myocardium both proximally and distally to the second conduit portion 244.

During diastole, the pressure in the left ventricle is at its minimum, approximately 5-10 mm Hg, while the pressure in the LAD is approximately 80 mm Hg. This pressure differential results in blood being drawn from the LAD into the left ventricle, which would seemingly counteract the delivery of blood to the LAD during systole. It is believed, however, that this backflow of blood into the left ventricle (which may be characterized as "steal" in that blood is being taken from the coronary artery) does not prevent adequate perfusion of the myocardial tissue fed by the distal LAD. In the case of a partial proximal obstruction in the LAD, any blood flowing from the aorta that is stolen into the left ventricle should not prevent adequate revascularization insofar as the aorta may be considered an infinite source. In the case of a complete obstruction in the LAD, any blood that is stolen into the left ventricle will be taken from the distal LAD; however, testing of the inventive conduits has shown that the myocardial tissue is adequately perfused despite a complete proximal obstruction in the LAD. Adequately perfused means that a threshold level of oxygenated blood is being delivered to the myocardial tissue to allow the heart to function within acceptable limits.

The conduits of the invention could be provided with a check valve to prevent backflow of blood into the left ventricle. This design, though, is presently not as preferred as a non-valved conduit. One significant benefit provided by a non-valved conduit is that blood flow through the conduit is essentially constant, although in different directions, which prevents hemostasis in the conduit. As such, not using a valve and allowing backflow through the conduit prevents or reduces the likelihood of thrombosis (clotting) in the conduit, which is a primary concern with any device (like a valve) that is placed in a blood flow path. Consequently, the washing effect provided by blood flowing through the conduit is believed to obviate thrombosis or thrombosis-related problems. This is in contrast to a valved conduit that closes during diastole and thus results in blood remaining stationary in the conduit during a phase of the heart cycle.

Figure 21A:
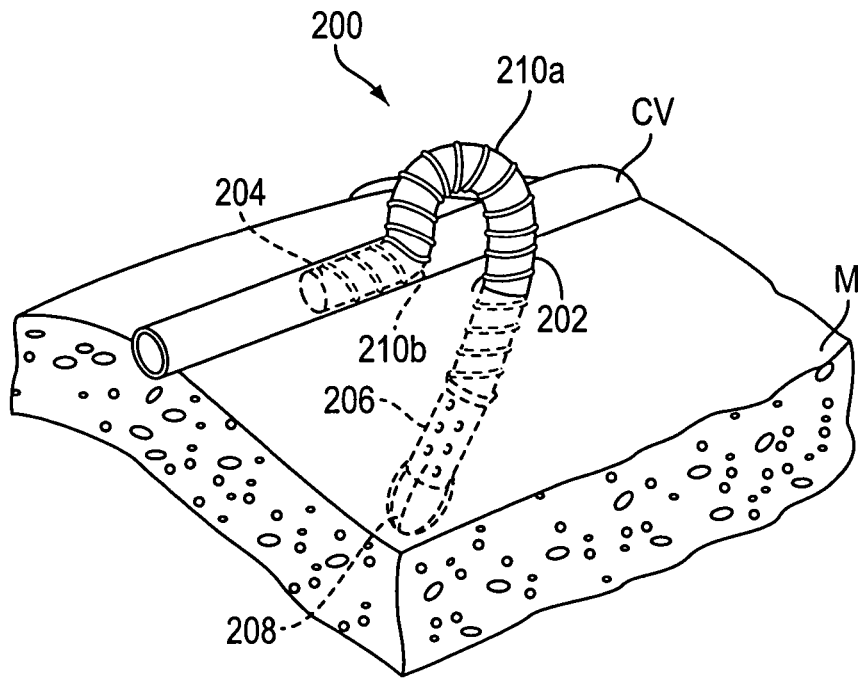
FIGS. 21A and 21B are perspective views of conduits constructed according to two embodiments of the invention deployed in a heart to communicate a coronary vessel with a heart chamber containing blood.
Figure 21B:
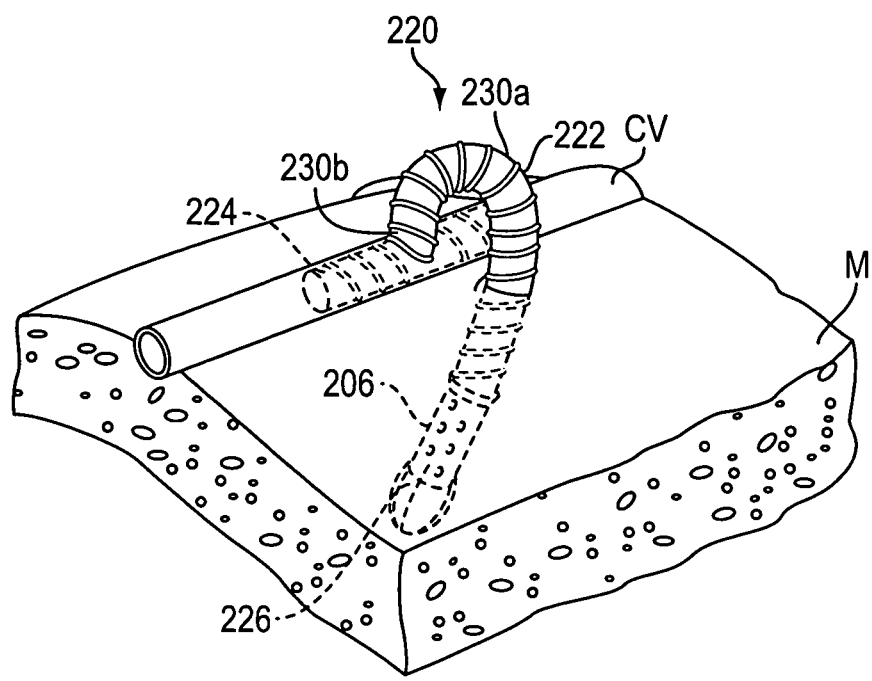
Figure 22A:
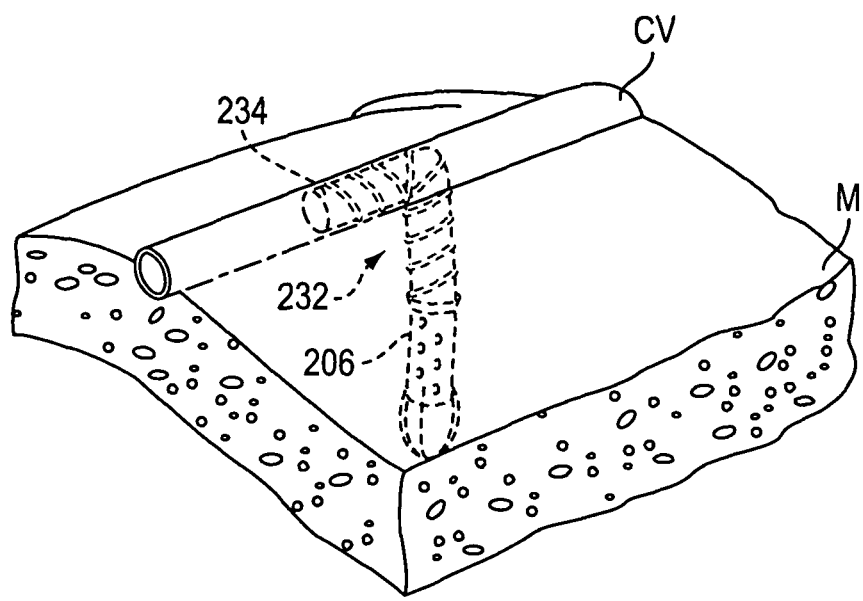
FIGS. 22A and 22B are perspective views of conduits constructed according to two other embodiments of the invention deployed in a heart to communicate a coronary vessel with a heart chamber containing blood.
Figure 22B:
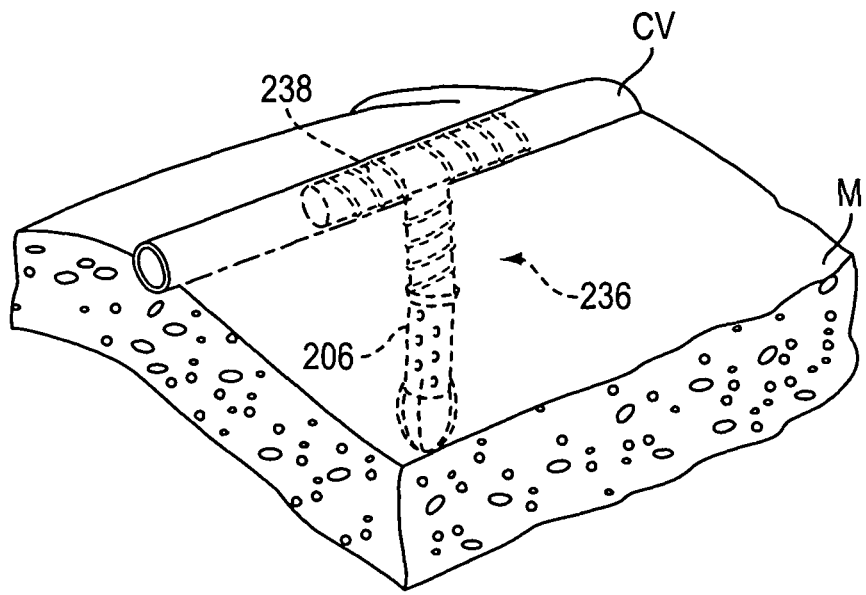

FIGS. 21A and 21B show the conduits 200, 220 of FIGS. 18A-18B and 19A-19B positioned in a coronary vessel CV with the device 206 in fluid communication with a heart chamber C containing blood. As shown, a significant portion of the length of each conduit 200, 220 is disposed external to the myocardium M; the relative length of material that is within tissue (transmural) and external may be varied from that shown. FIGS. 22A and 22B show alternative conduit configurations wherein substantially all of the length of the conduit is disposed within tissue. FIG. 22A shows a conduit 232 with a portion 234 located in a coronary vessel, another portion of the conduit 232 including a device 206 in communication with a heart chamber C. FIG. 22B shows a conduit 236 having a target vessel portion 238 located in a coronary vessel, with another portion of the conduit 238 provided with a device 206 for communicating with the heart chamber C. Other conduit configurations may be used as well; for example, the partial tubular conduits shown in FIGS. 4 and 5 may be used in a transmural application such as those shown in FIGS. 22A and 22B.

Figure 23:
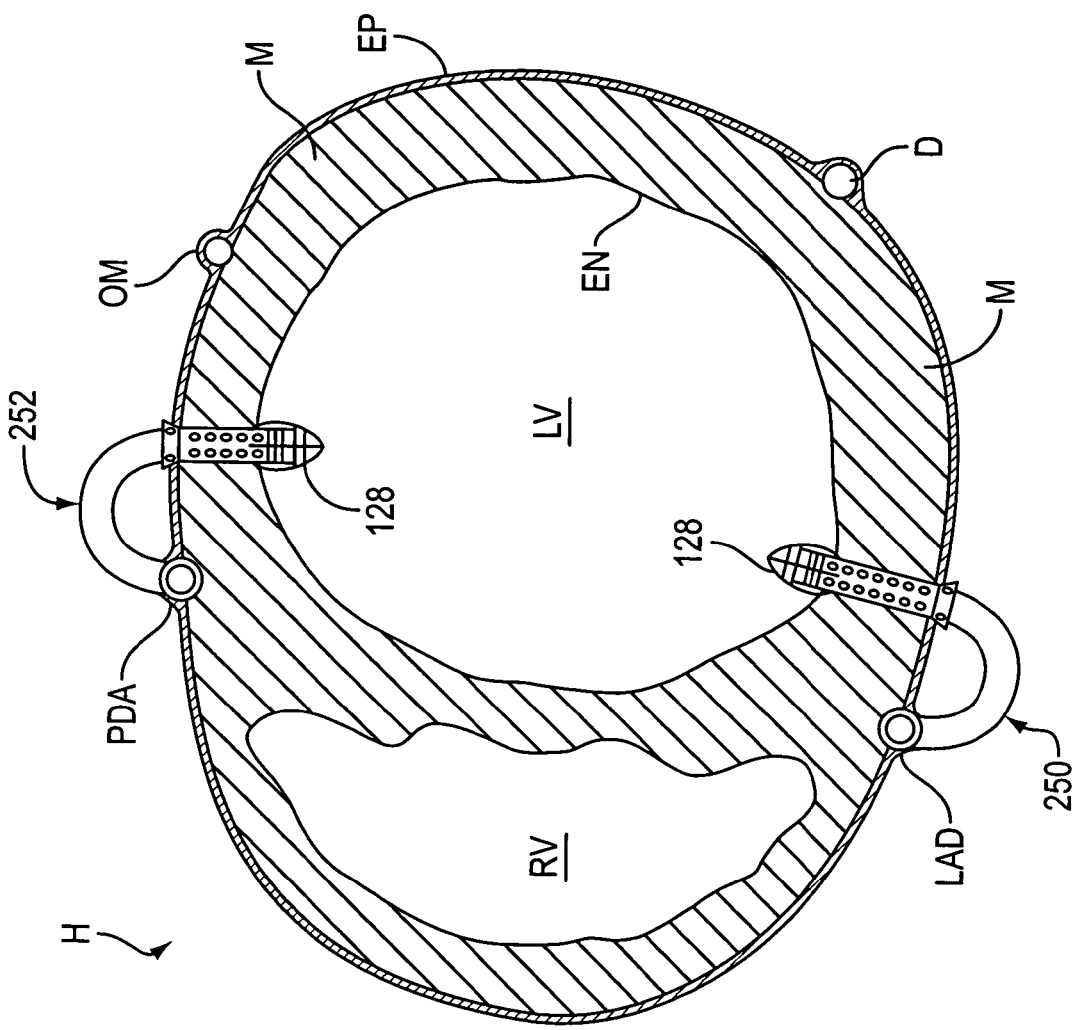
FIG. 23 is a transverse sectional view of a heart showing the left and right ventricles and several coronary blood vessels.

As noted above, the LAD is only one example of a coronary vessel that may be treated according to the invention. FIG. 23 is a sectional view of the heart H shown in FIG. 20C, taken along a generally horizontal line cutting through the myocardium and the LAD. The section line extends distal to the diagonal D, and the perspective of FIG. 23 is looking down toward the apex of the heart. This view shows the LAD and one of its diagonal branches D, the posterior descending branch, PDA, of the right coronary artery RCA, and the obtuse marginal branch, OM, of the circumflex artery.

A conduit 250 is shown deployed to communicate the left ventricle LV and the LAD, while a conduit 252 is shown deployed so as to communicate the left ventricle LV and the PDA. The conduits 250, 252 are constructed as described above with respect to previous embodiments and include devices 128 that penetrate the epicardium EP, the endocardium EN and the myocardium M to communicate with the left ventricle LV. Those skilled in the art will appreciate that the diagonal D and the obtuse marginal OM represent additional coronary vessels that could be coupled to conduits placed in communication with the left ventricle LV. As such, it will be recognized that the target vessels shown in FIG. 23 are exemplary only.

Figure 24A:
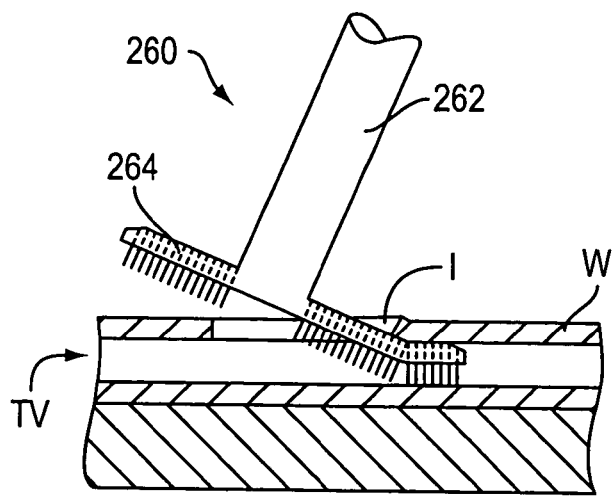
FIGS. 24A-24D are elevation views, partly in section, schematically illustrating placement of a conduit in a target vessel according to one embodiment of the invention.
Figure 24B:
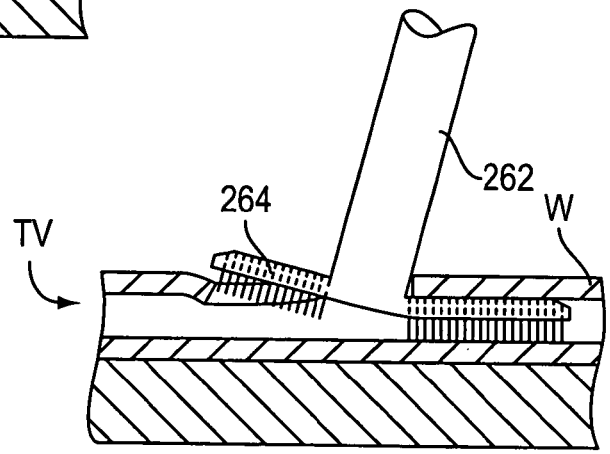
Figure 24C:
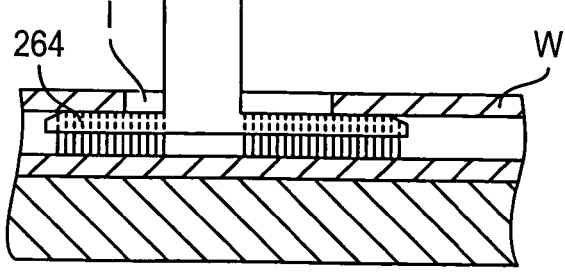

The conduit of the invention may be introduced into the lumen of the target vessel via any suitable means. One preferred method is shown in FIGS. 24A-24D and comprises surgically forming an incision I in the wall W of a target vessel TV for receiving a conduit 260 including first and second conduit portions 262, 264. The conduit 260 is similar to the conduit 30 of FIGS. 4-4A, except only the second conduit portion 264 is provided with a reinforcing component. A distal end of the second conduit portion 264 is inserted through the incision (FIG. 24A) and into the vessel lumen. In this embodiment, the distal end of the second conduit portion 264 is moved distally a sufficient distance to center or substantially center the conduit 260 in the vessel (FIG. 24B). The proximal end of the second conduit portion 264 is then pushed into the vessel lumen (24C), which results in both legs of the second conduit portion 264 being in the lumen and away from the ends of the incision. This affixes the conduit 260 to the target vessel TV and preferably provides a fluid-tight seal.

It will be noted that the conduit 260 is deployed to its final position without substantially moving the second conduit portion 264 within the target vessel lumen. That is, the conduit is not moved relative to the vessel wall by an amount that risks damaging the intimal surface of the vessel wall. Alternatively, the conduit may be deployed by sliding the distal end of the second conduit portion distally, placing the proximal end in the vessel lumen, and sliding the conduit proximally to anchor it to the vessel (in a manner somewhat similar to that used by surgeons to place a perfusion bridge in a coronary artery during cardiac surgery).

Figure 24D:
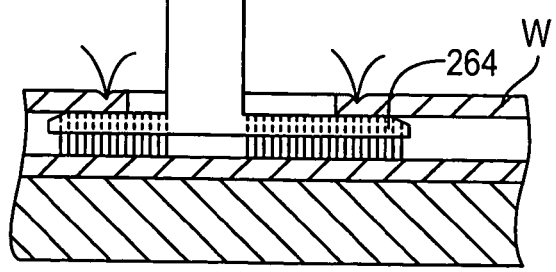

The second conduit portion 264 will remain in location in the target vessel due to the anchoring provided by the proximal and distal legs of the second conduit portion 264. The attachment between the conduit and the target vessel should provide a hemostatic seal; therefore, if necessary, additional means for securing the conduit to the vessel may be used, for example, suture (as shown in FIG. 24D), fasteners, clamps, clips, cuffs, gasket-like structures and fibrin or collagen-based adhesives and sealants.

Figure 25A:
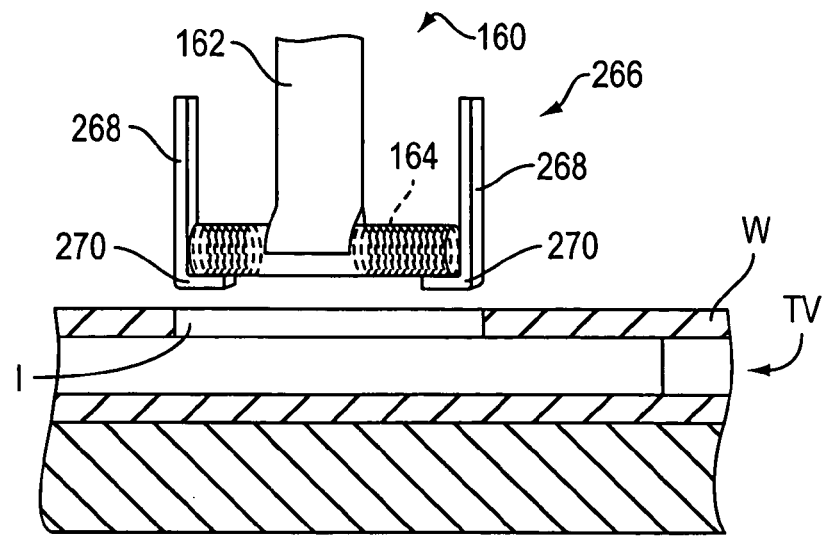
FIGS. 25A-25C are elevation views, partly in section, schematically illustrating placement of a conduit in a target vessel according to another embodiment of the invention.
Figure 25B:
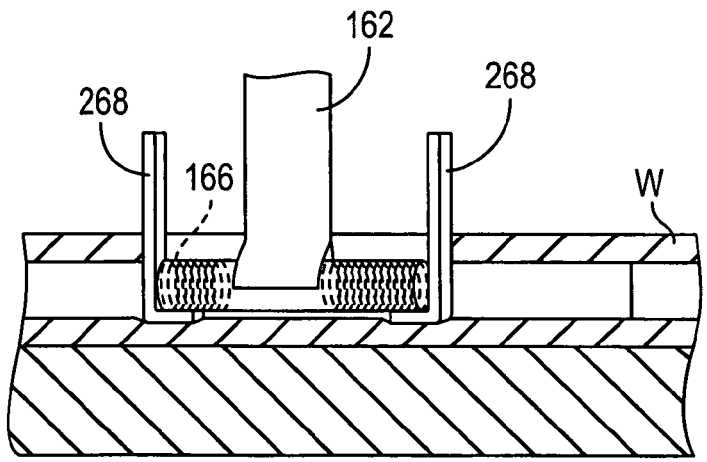
Figure 25C:
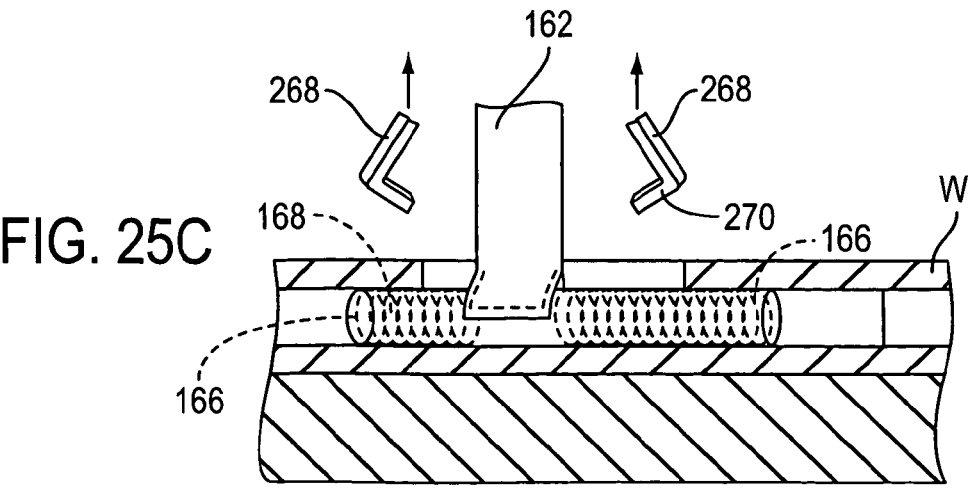

FIGS. 25A-25C illustrate an exemplary method for deploying a collapsible conduit 160 which has been described above with respect to FIGS. 13A-13B. Briefly, the conduit 160 includes first and second conduit portions 162, 164, the latter defining free ends 166 provided with a reinforcing component 168. The reinforcing component 168 allows the second conduit portion 164 to collapse along (or substantially along) the longitudinal axis of the portion 164, which preferably generally coincides with the longitudinal axis of the target vessel.

FIG. 25A schematically shows a retaining instrument 266 for holding the second conduit portion 164 in its collapsed orientation. The retaining instrument 266 is a forceps-type device with a pair of arms 268 for holding the conduit. The arms 268 have jaws 270 that engage the free ends 166 of the second conduit portion 164 and retain the reinforcing component 168 collapsed while placed through an incision I formed in the wall W of a target vessel TV. FIG. 25B shows the arms 268 and the second conduit portion 164 disposed in the lumen of the target vessel while still collapsed. The arms 268 are removed, as shown in FIG. 25C, which allows the reinforcing component 168 and the second conduit portion 164 to assume their expanded orientation in engagement with the wall of the target vessel, thereby securing the conduit 160 to the target vessel. Other means may of course be used to hold the conduit collapsed, for example, an instrument that engages the interior of the conduit to restrain the second conduit portion 164.

Figure 26A:
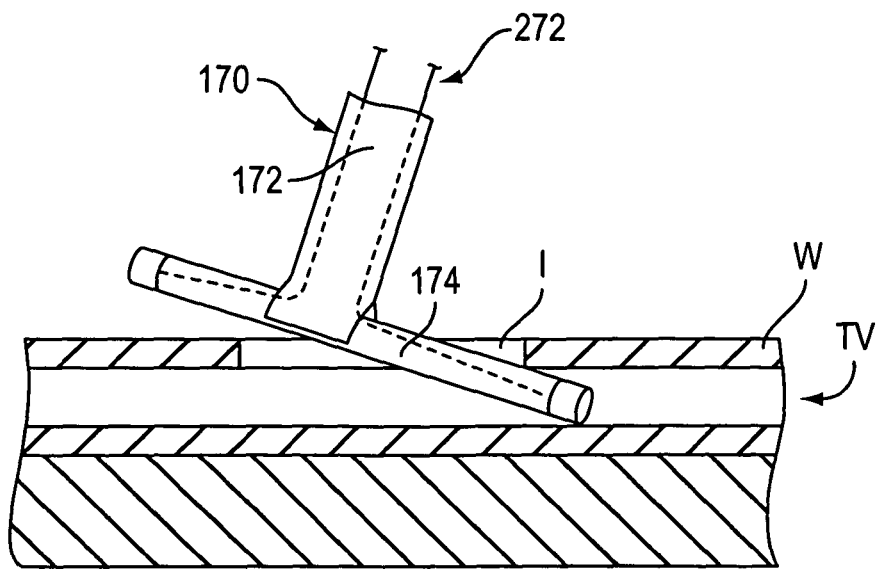
FIGS. 26A-26C are elevation views, partly in section, schematically illustrating placement of a conduit in a target vessel according to yet another embodiment of the invention.
Figure 26B:
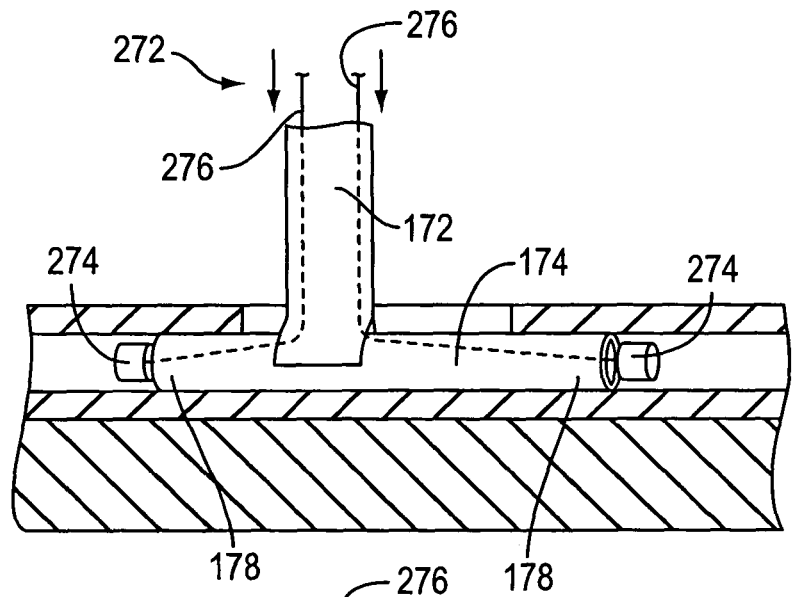
Figure 26C:
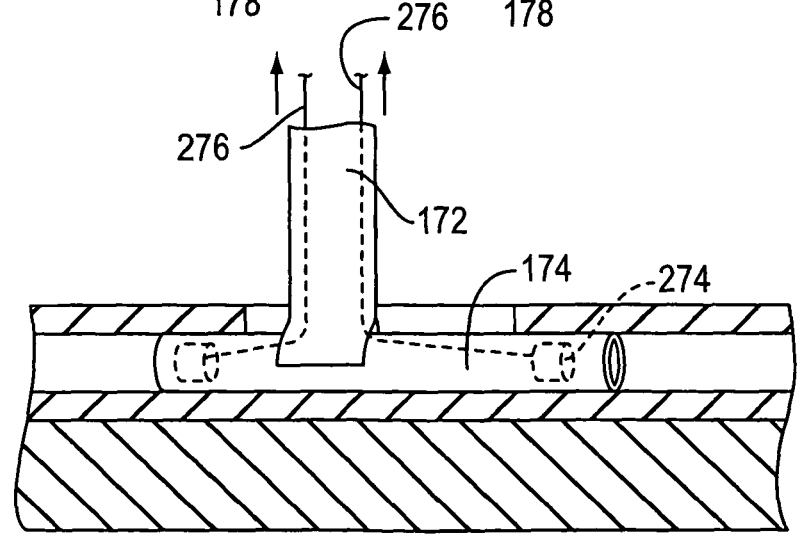

FIGS. 26A-26C illustrate another exemplary method for deploying a collapsible conduit 170 in a target vessel, the conduit 170 having been described above with respect to FIGS. 14A-14B. The conduit 170 has first and second conduit portions 172, 174, but does not include a reinforcing component. The second conduit portion 174 is collapsible about (or substantially about) the longitudinal axis of the portion 174, i.e., it is radially collapsible. In FIG. 26A, a retaining instrument 272 holds the second conduit portion 174 in its collapsed orientation. The retaining instrument 272 includes two elements 274 that engage the collapsed ends 178 of the second conduit portion 174. The elements 274 are cup-shaped to receive the folded ends 178 of the conduit, and are connected to and manipulated by a pair of shafts 276.

FIG. 26A shows the second conduit portion 174 held collapsed by the retaining instrument 272 while being introduced through an incision I in the wall W of a target vessel TV. FIG. 26B shows the second conduit portion 174 disposed in the vessel lumen with, as indicated by the arrows, the shafts 276 being moved toward the vessel to separate the elements 274 from the conduit ends 178. As shown, this allows the second conduit portion 174 to assume its expanded orientation (which is larger in cross-section than the elements 274). Once the second conduit portion 174 has been expanded, the shafts 276 are moved as shown to remove the elements 274 through the first conduit portion 172. The incision I may then be sutured and sealed, as explained above.

The collapsible conduit retaining instruments 266 (FIGS. 25A-25D) and 272 (FIGS. 26A-26C) are depicted somewhat schematically as they are only intended to represent some of the various devices that may be used to deploy a collapsible conduit according to the invention. For example, a delivery device may include a sheath(s) that retains a portion of the conduit collapsed. The delivery device could incorporate other removable securing means, such as suture, to retain the conduit in its collapsed state. Accordingly, it will be recognized that this aspect of the invention may be practiced independently of any particular type of introducing instrument.

Figure 27:
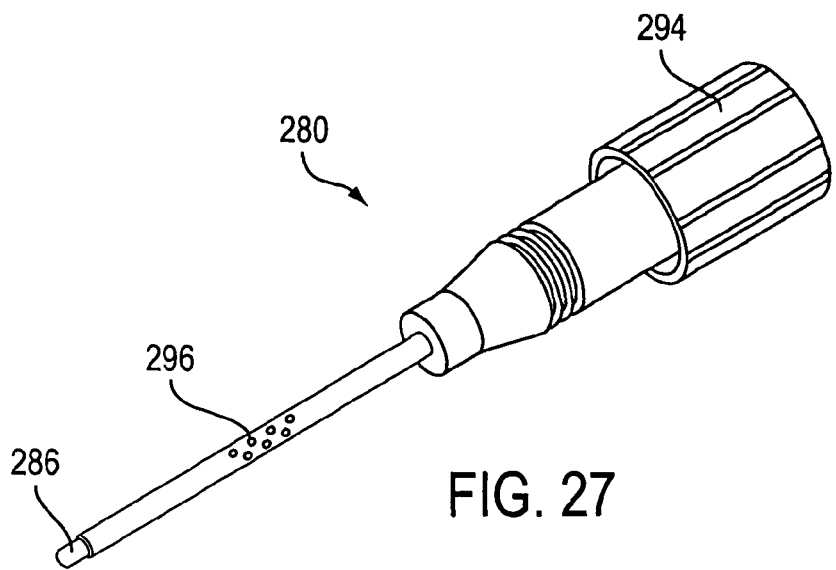
FIG. 27 is a perspective view of a device constructed according to another embodiment of the invention for use in perfusing a target vessel while introducing a conduit into the vessel.

Another embodiment of a device and method for deploying a conduit in a target vessel according to the invention will be described with respect to FIGS. 27-29A and 30A-30E. FIG. 27 shows a delivery device indicated by the reference numeral 280 for use in deploying a conduit in a target vessel while maintaining some level of perfusion during deployment. The device 280 is used to introduce a conduit into the lumen of the target vessel, the conduit being coupled to a source of blood that will be delivered to the vessel upon attachment of the conduit to the vessel. As a result, this embodiment of the invention minimizes ischemic time during deployment by perfusing the target vessel distally of the attachment site between the conduit and the vessel.

Figure 28:
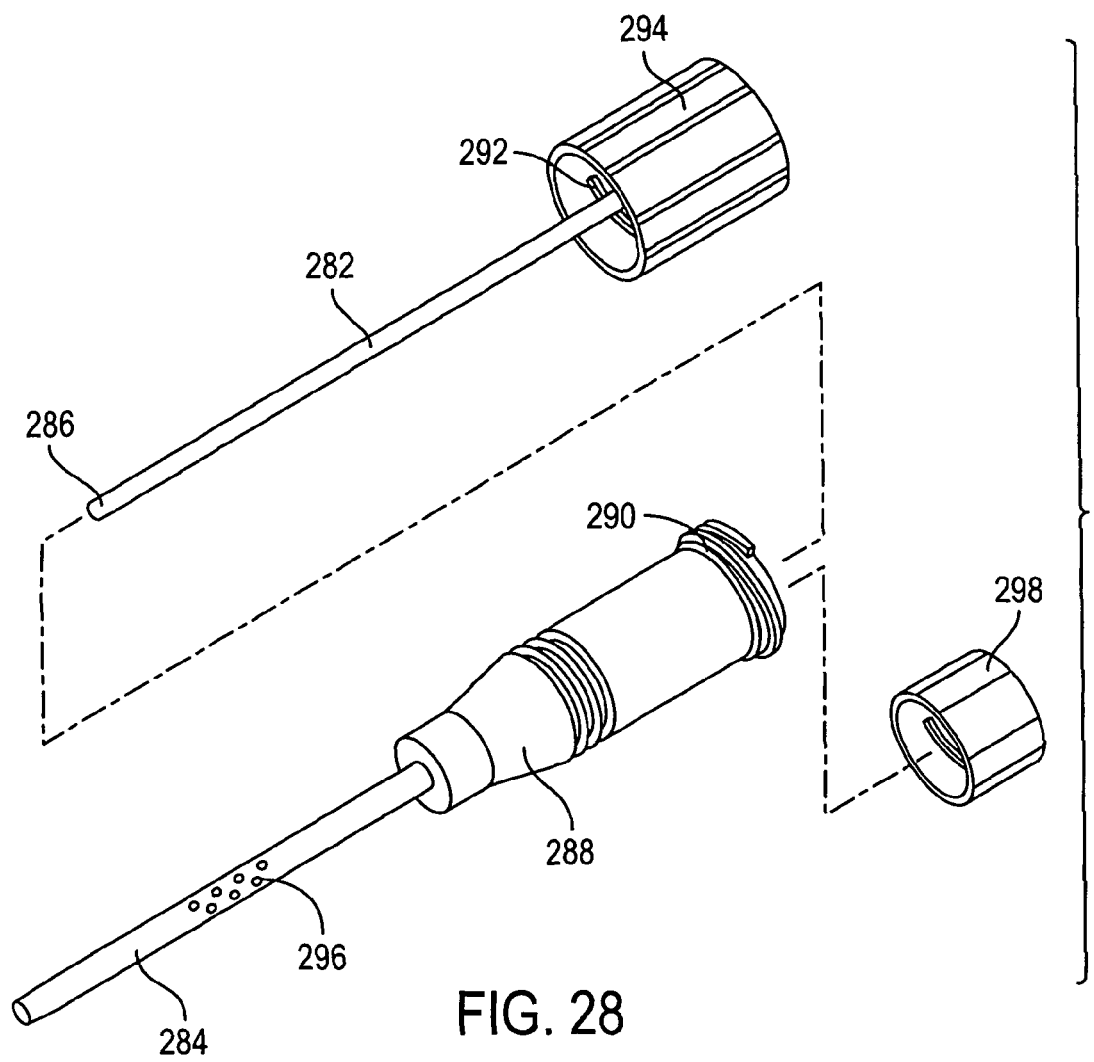
FIG. 28 is an exploded perspective view of the device shown in FIG. 27, along with an additional member for sealing the device.
Figure 29A:
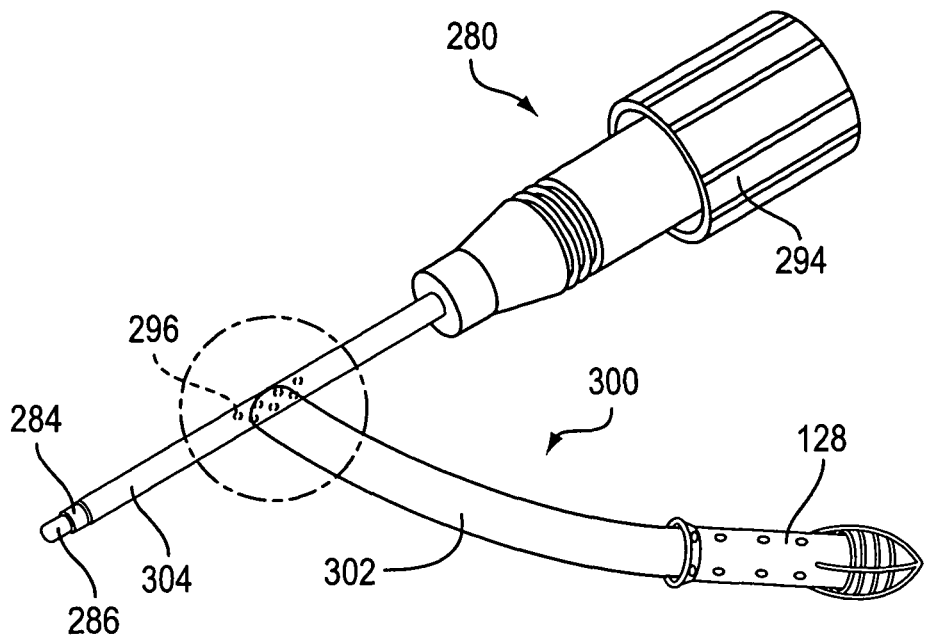
FIG. 29A is a perspective view of the device shown in FIG. 27 with a conduit mounted thereon.

The delivery device 280 includes an inner component preferably in the form of an obturator 282 and an outer component preferably in the form of a sheath 284 (FIG. 28). The obturator 282 is movable with respect to the sheath 284. The obturator 282 has a distal end 286 that slightly projects beyond the distal end of the sheath 284, as shown in FIG. 27. The sheath has a hub 288 with threads 290 for engaging the threads 292 carried by a cap 294 mounted to the obturator 282. The distal end portions of the obturator 282 and the sheath 284 are preferably tapered and have complementary shapes that provide a smooth transition for atraumatic insertion into the target vessel. The threads 290, 292 provide a quick turn luer-type connection, although non-threaded attachment mechanisms may be used. The sheath 284 has one or more openings 296 passing into the sheath interior, these openings being blocked when the obturator 282 is within the sheath 284 (FIG. 29A). FIG. 28 also shows a cap 298 that may be attached to the sheath hub 288 to seal the hub after removing the obturator 282.

Figure 29B:
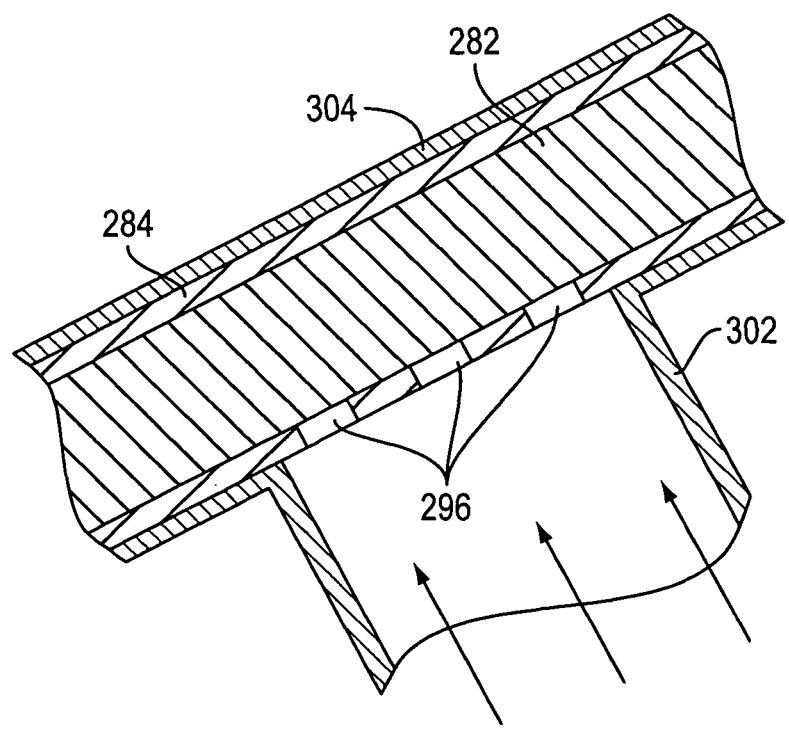
FIG. 29B is an enlarged sectional view of the portion encircled in FIG. 29A.

FIG. 29 shows the delivery device 280 of FIGS. 27-28 supporting a conduit 300 constructed according to the invention. The conduit 300 includes first and second conduit portions 302, 304 and a device 128 configured to be placed in communication with a heart chamber containing blood, as described above. The second conduit portion 304 is mounted on the sheath 284 with the proximal end (to the right in FIG. 29) of the conduit portion 304 abutting the sheath hub 288, which holds the conduit 300 in position during delivery. In FIG. 29A blood flowing from a source (not shown) to the conduit 310 is indicated by arrows. As can be seen, blood flowing through the first conduit portion 302 is prevented from entering the lumen of the sheath 284 because the sheath openings 296 are blocked by the obturator 282. As such, the first conduit portion 302 may be coupled to the blood source and the second conduit portion 304 mounted on the device 280 and manipulated without leakage of blood.

Figure 30A:
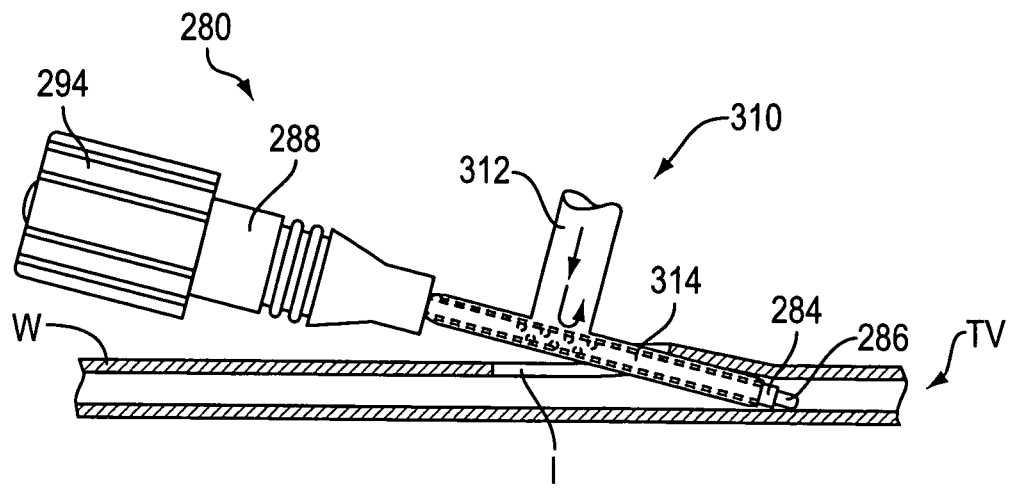
FIGS. 30A-30E are elevation views in section schematically illustrating the device and conduit shown in FIGS. 29A-29B being used to place the conduit in fluid communication with the lumen of a target vessel.

FIGS. 30A-30E depict an illustrative method of using the delivery device 280 to introduce and deploy a conduit in a target vessel according to the invention. FIG. 30A shows a conduit 310 including first and second conduit portions 312, 314 respectively adapted to be communicated with a source of blood and a target vessel. The source of blood is indicated schematically as it will be appreciated any suitable source may be used, e.g., a heart chamber, the aorta, a coronary artery or vein, a peripheral artery or vein, etc. Similarly, the target vessel TV may be a coronary artery or vein, a peripheral artery or vein, or any other luminal body structure.

Figure 30B:
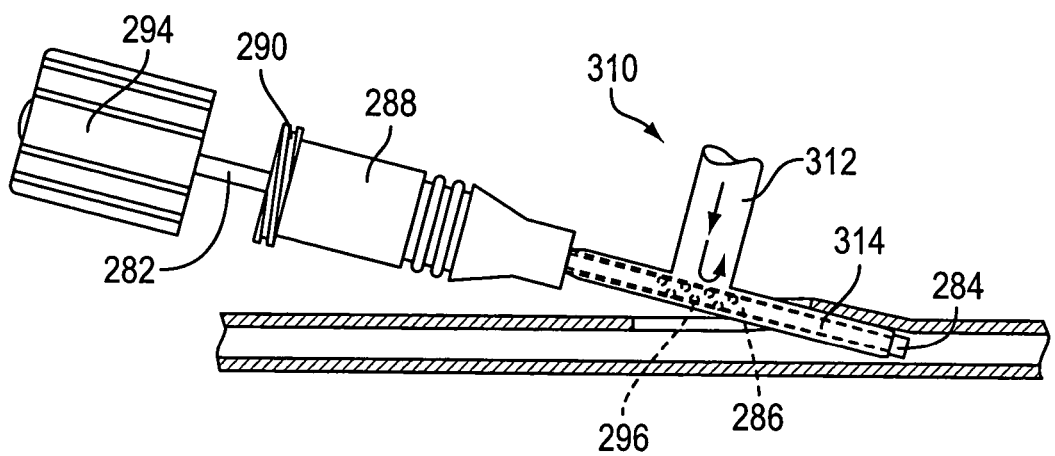

FIG. 30A shows the distal end portion of the device 280 inserted through an incision I in a target vessel wall W so as to place the distal end 316 of the second conduit portion 312 within the vessel lumen. The soft atraumatic end 286 of the obturator minimizes any tissue damage during introduction. In FIG. 30A, the obturator 282 blocks the sheath openings 296 such that blood flowing from the source through the first conduit portion 310 is prevented from entering the sheath 284, as indicated by the arrows. FIG. 30B shows the next step, removing the obturator from the sheath 284 by moving the obturator cap 294 proximally. The distal end 286 of the obturator must clear one or more of the sheath openings 296 in order for blood from the source to flow through the first conduit portion 310 and into the sheath 284. At the position depicted in FIG. 30B, the obturator 282 still blocks the sheath openings 296.

Figure 30C:
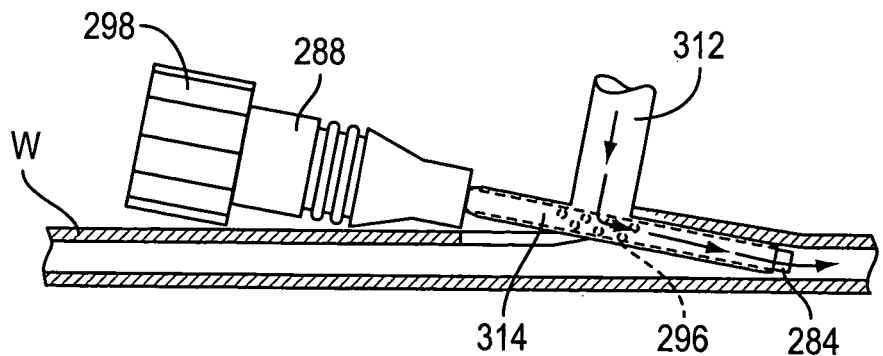

FIG. 30C shows the delivery device 290 after the obturator 282 has been removed. As indicated by the arrows, blood from the source is now free to enter the sheath lumen via openings 296 and flow distally into the target vessel as it passes out the end of the sheath 284. As a result, despite the fact that minimal steps have been performed and the conduit 310 has not been fully deployed in or secured to the target vessel, the delivery device 290 enables perfusion of the distal vasculature. Hence, the remaining delivery steps may be carried out with less risk of the tissue perfused by the target vessel becoming ischemic during the procedure, a significant benefit in a coronary bypass procedure.

FIG. 30C also shows the cap 298 secured to the sheath hub 288 to seal the sheath lumen and prevent blood from exiting the proximal end of the sheath. The cap 298 may have a mechanism that seals around instruments introduced into the sheath 284 and/or secures the instrument to the sheath 284 and the cap 298. Any suitable mechanism may be used, e.g., a Tuohy-Borst compression adapter or a self-sealing septum.

Figure 30D:
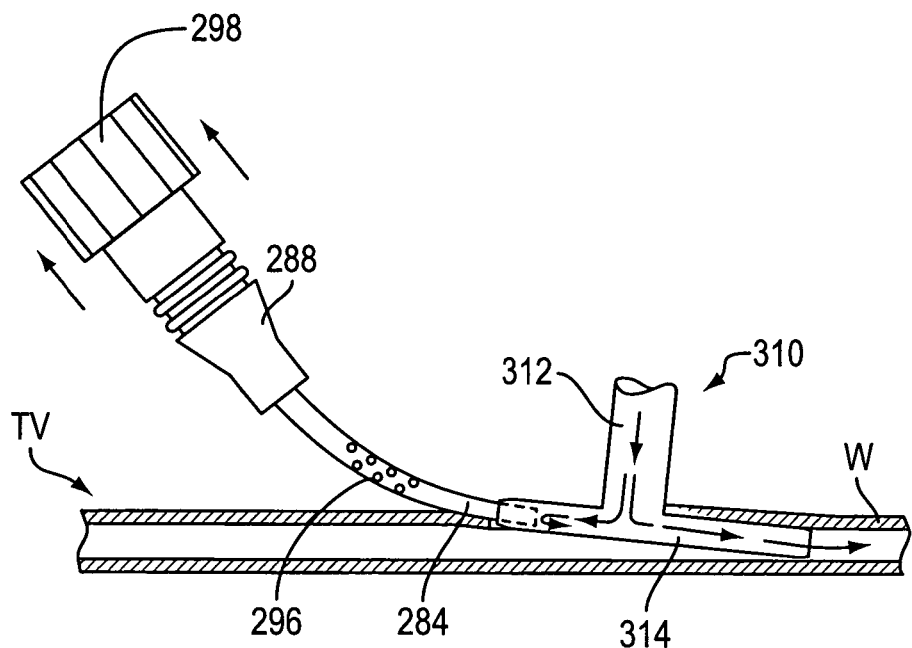
Figure 30E:
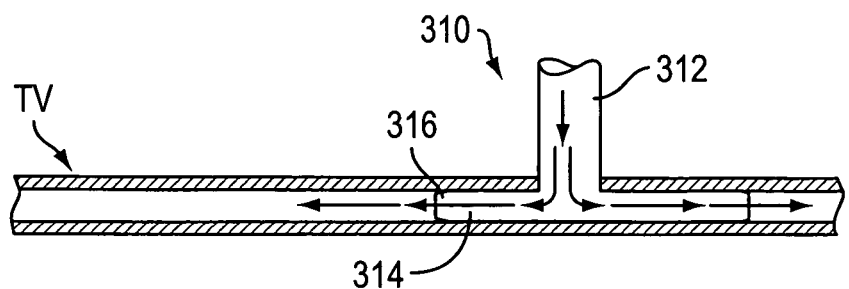

FIG. 30D shows the delivery device 290 being moved proximally to separate the sheath 284 from the second conduit portion 314, during which blood from the source continues to flow distally and perfuse the distal vasculature. Upon completely removing the sheath 284 from the second conduit portion 312 (or as the sheath is being removed), the proximal end 316 of the conduit portion 312 is moved into the target vessel lumen, as shown in FIG. 30E. This placement of the conduit 310 results in blood from the source being delivered in multiple directions which, in FIG. 30E, are proximal and distal along the longitudinal axis of the vessel, as indicated by the arrows.

A variation of the delivery device shown in FIGS. 30A-30E utilizes a hollow obturator with one or more openings passing into a lumen. The sheath is omitted in this embodiment, and blood from the source flows through the second conduit portion, through the opening(s), and into the target vessel. The opening may be a slot extending along a portion of the length of the hollow obturator so that rotating the obturator within the first conduit portion moves the slot into or out of alignment with the second conduit portion. In this manner, the device can be controlled, preferably from a proximal location, by rotating (or otherwise manipulating) the shaft to selectively allow or block flow into the hollow obturator.

The conduit of the invention is preferably sized and configured to form a blood flow path that is equal or substantially equal to the blood flow path defined by the native vessel. In other words, the conduit preferably defines an inner diameter that equals or substantially equals (e.g., 90% of) the inner diameter of the native vessel. As a result, when placed in the target vessel the conduit allows a sufficient volume of blood flow. If the target vessel is a coronary artery, this ensures that blood will flow to the distal vasculature and perfuse the myocardial tissue.

The overall size and relative dimensions of the conduit will vary depending on the application. For sake of example, with reference to FIGS. 1, 1B and 2, it can be seen that the length and diameter of the first conduit portion 12 are greater than the length L2 and diameter D2 of the second conduit portion 14. As an example, the length L1 of the first conduit portion 12 may be within a range of from about 20 mm to 80 mm, and more preferably a range of from about 30 mm to 50 mm, while the length L2 of the second conduit portion 14 is preferably within the range of 3 mm to 20 mm, and more preferably within the range of 5 mm to 15 mm. When deployed in the application shown in FIG. 21, for example, approximately 25 mm of conduit (including the portion extending into the hear chamber) is placed in the myocardium, approximately 15 or 16 mm of conduit is placed in the coronary vessel, and approximately 15 mm extends externally to the myocardium.

Similarly, the diameter D1 (and in particular the inner diameter) of the first conduit portion 12 may vary but is preferably within the range of from about 2 mm to 10 mm, and more preferably within the range of from 3 mm to 4 mm. The diameter D2 of the second conduit portion 14 will be dictated primarily by the size of the lumen of the target vessel being treated. As an example, for use in coronary vessels, the diameter D2 (and in particular the inner diameter) of the second conduit portion 14 is preferably within the range of 1 mm to 4 mm. It will be recognized, however, that these ranges are exemplary as the invention encompasses conduits the dimensions of which fall outside such ranges by an amount that will not preclude their use in a desired application (cardiovascular or other).

The conduit of the invention also may be characterized by the relative dimensions of the respective conduit portions. For example, with reference to FIG. 2, if the length L2 of the second conduit portion 14 is greater than D1, then some of the second conduit portion disposed in the target vessel lumen will extend beyond the ends of the incision (not shown in FIGS. 1-2). In an application involving a coronary artery as the target vessel, the ratio of the diameter D1 (and in particular the outer diameter) of the first conduit portion 12 to the length L2 of the second conduit portion 14 (D1/L2) is preferably within a range of from about 1:1 to about 1:10, and more preferably within the range of from about 1:2 to about 1:4.

The conduit of the invention may be manufactured by various processes. It is currently preferred to mold the conduit of (or fabricate the conduit from) a material having desired blood interface qualities as well as a desired combination of flexibility and column strength. Manufacturing processes and materials for forming the conduits disclosed herein are disclosed in co-pending, commonly owned application Ser. No. 09/394,119, filed on Sep. 10, 1999 and entitled "Methods and Devices for Manufacturing a Conduit for Use in Placing a Target Vessel in Fluid Communication With a Source of Blood," the entire subject matter of which application is incorporated herein by reference.

The type of procedure (e.g., open chest, minimally invasive, percutaneous, etc.) that is used to deploy the conduit of the invention may vary depending on the vessels being treated and user preference. As an example, a minimally invasive procedure may be used to deploy the conduit on a beating heart using various devices and methods for stabilizing all or a portion of the heart. Also, the conduits may be coupled to the target vessel other than as specifically shown herein. While several collapsible conduits are illustrated along with exemplary methods for deploying them in a target vessel, it will be appreciated that the invention encompasses securing non-collapsible conduits to the vessel. For instance, the second conduit portion may be a non-collapsible, tubular member that is placed in the target vessel lumen after first dilating the vessel wall, and then is retained by allowing the vessel wall to move back and snugly engage the exterior of the second conduit portion.

Moreover, the conduit may be used with a component that secures and preferably seals the conduit to the wall of the target vessel. For example, the component could comprise a sleeve or cuff member that partially or completely surrounds the conduit adjacent the target vessel wall. The vessel wall is effectively sandwiched between the component and the intraluminal portion of the conduit, i.e., the conduit portion located in the vessel lumen (the second conduit portion in the above embodiments). The component exerts sufficient force toward the intraluminal portion of the conduit to secure the assembly to the target vessel while providing adequate hemostasis at the attachment site. The component could be separate from or integral with the conduit, and could be constructed according to the teachings of co-pending, commonly owned application Ser. No. 09/393,130, filed on Sep. 10, 1999 and entitled "Anastomotic Methods and Devices for Placing a Target Vessel in Fluid Communication With a Source of Blood," the entire subject matter of which application is incorporated herein by reference.

It should also be noted that the conduits of the invention may be introduced into a target vessel in various ways. For example, in the illustrated embodiment, the second conduit portion is inserted through a surgical incision in the vessel wall. An alternative arrangement includes a delivery device on which the conduit is mounted, the device having a permanent or detachable incising element with a sharpened tip for penetrating the wall of the target vessel in conjunction with introducing the conduit. Another arrangement uses a sheath that restrains a collapsible conduit and is removed to deploy the conduit.

Additionally, the conduits of the invention are preferably, though not necessarily, placed with the portion in the myocardium spaced from the portion in the coronary vessel. That is, the channel passing through the myocardium is not beneath or immediately adjacent the vessel. Nonetheless, as shown above the conduit may be positioned transmurally in myocardial tissue directly or substantially beneath or adjacent the vessel. One benefit of the former method is that the conduit (or delivery device supporting the conduit) is introduced through the outer or anterior vessel wall to engage the lumen; it is not passed through the inner or posterior vessel wall, which tends to be more diseased than the outer wall.

It may be desirable to utilize a conduit delivery device having a portion surrounding the conduit to protect the conduit material prior to and during deployment. The device may have a bore that, in addition to receiving the aforementioned optional incising element so that may be extended and retracted, is configured to act as a flashback lumen and indicate when the device has entered a lumen containing blood, for example, a coronary artery or heart chamber. Of course, additional members, for example, a guide wire or guide catheter, may be used to deliver the conduit.

The conduits of the invention may be provided with a valve or other means for controlling or regulating blood flow. Suitable valves, as well as means for measuring myocardial thickness or verifying entry into the heart chamber, are disclosed in application Ser. No. 09/023,492, filed on Feb. 13, 1998, and entitled "Methods and Devices Providing Transmyocardial Blood Flow to the Arterial Vascular System of the Heart," the entire subject matter of which has been incorporated herein by reference. Likewise, the conduits may be provided with a reservoir for retaining and discharging blood in a desired manner.

The conduits and delivery devices of the invention may be sized and configured differently from that specifically illustrated in the Figures. For instance, the cross-section of one or more portions of the conduit may be noncircular, e.g., elliptical to better match the profile of the target vessel. As a further example, the delivery device may be relatively short with the shaft assembly substantially rigid for use in an open-chest procedure. Alternatively, the device may be configured for use in either a minimally invasive or endosvascular procedure, wherein the actuators for controlling the device components are located adjacent the proximal end of the device to allow remote deployment of the conduit, for example, as disclosed in the aforementioned, co-pending, commonly-owned application Ser. No. 09/304,140.

It will be appreciated that the features of the various preferred embodiments of the invention may be used together or separately, while the illustrated methods and devices may be modified or combined in whole or in part. As an example, more than one conduit may be coupled to a manifold that is placed in communication with one source of blood so as to deliver blood to multiple target vessels. The conduits and devices of the invention may include removable or detachable components, could be formed as disposable instruments, reusable instruments capable of being sterilized, or comprise a combination of disposable and reusable components.

Further, it will be understood that the embodiments may be used in various types of procedures, for example, an open surgical procedure including a median sternotomy, a minimally invasive procedure utilizing one or more relatively small access openings or ports, or an endovascular procedure using peripheral access sites. Also, endoscopes or thoracoscopes may be used for visualization if the procedure is performed through very small ports. The different embodiments may be used in beating heart procedures, stopped-heart procedures utilizing cardiopulmonary bypass (CPB), or procedures during which the heart is intermittently stopped and started.

It will be recognized that the invention is not limited to the illustrated applications. For example, the inventive conduits may be used in a CABG procedure by being coupled to an autologous conduit, e.g., a saphenous vein graft (or a nonautologous vessel such as a xenograft, etc.). Further, the conduit could be coupled to a native artery, such as one of the internal mammary arteries, and then secured to the target vessel. Further still, the conduit may be coupled to an existing CABG graft that has partially or completely occluded over time by plugging the second conduit portion into the wall of the graft to communicate with the graft lumen distal to the occlusion.

It will be recognized that the invention may be used to manufacture conduits the use of which is not limited to cardiovascular applications such as those illustrated and discussed above. For example, the invention may be used to produce conduits used to carry out many different bypass procedures, including, without limitation, femoral-femoral, femoral-popliteal, femoral-tibial, ilio-femoral, axillary-femoral, subclavian-femoral, aortic-bifemoral, aorto-iliac, aorto-profunda femoris and extra-anatomic. The conduit may be used to establish fluid communication with many different vessels, including, without limitation, the renal arteries, mesenteric vessel, inferior mesenteric artery, eroneal trunk, peroneal and tibial arteries. Still other applications for the invention include arteriovenous shunts. The conduit may have one, both or more ends configured to engage a target vessel for receiving blood from or delivering blood to another vessel.

The preferred embodiments of the invention are described above in detail for the purpose of setting forth a complete disclosure and for sake of explanation and clarity. It will be readily understood that the scope of the invention defined by the appended claims will encompass numerous changes and modifications.

What is claimed is:

1. A device for placing a target vessel of a patient's vascular system in fluid communication with a heart chamber containing blood by forming a blood flow path between the target vessel and the heart chamber, the device comprising:

a conduit having first and second portions each of which has an axis, the axes of the first and second conduit portions being transverse to each other;

wherein the first conduit portion has a free end and is configured to be placed in fluid communication with a heart chamber containing blood, and the second conduit portion has two free ends that are sized and configured to be positioned at least partially within the lumen of a target vessel in the patient's vascular system;

wherein a diameter of the first conduit portion is greater than a diameter of the second conduit portion, and a channel defined by the first conduit portion is fluidly connected to a channel defined by the second conduit portion;

wherein the conduit is formed at least in part of a molded thermoset material having a predetermined amount of flexibility to permit the second portion of the conduit to be flexed for placement within the lumen of a target vessel;

wherein the first conduit portion includes a member configured to be placed in myocardial tissue without collapsing during myocardial contraction;

wherein the conduit is generally T-shaped and the first conduit portion corresponds to one leg of the T having one free end while the second conduit portion corresponds to another leg of the T having two free ends, and wherein the two free ends of the other leg of the T define first and second outlets adapted to be placed in fluid communication with the lumen of the target vessel; and wherein the second conduit portion conduit is configured such that the outlets may be disposed and secured within the lumen of the target vessel without the second conduit portion contacting the entire circumference of the inner vessel wall.

2. The device of claim 1, wherein the second conduit portion is generally semicircular in cross-section so as to leave the inner wall of the target vessel substantially uncovered.

3. A device for placing a target vessel of a patient's vascular system in fluid communication with a heart chamber containing blood by forming a blood flow path between the target vessel and the heart chamber, the device comprising:

a conduit having first and second portions each of which has an axis, the axes of the first and second conduit portions being transverse to each other;

wherein the first conduit portion has a free end and is configured to be placed in fluid communication with a heart chamber containing blood, and the second conduit portion has two free ends that are sized and configured to be positioned at least partially within the lumen of a target vessel in the patient's vascular system;

wherein a diameter of the first conduit portion is greater than a diameter of the second conduit portion, and a channel defined by the first conduit portion is fluidly connected to a channel defined by the second conduit portion;

wherein the conduit is formed at least in part of a molded thermoset material having a predetermined amount of flexibility to permit the second portion of the conduit to be flexed for placement within the lumen of a target vessel;

wherein the first conduit portion includes a member configured to be placed in myocardial tissue without collapsing during myocardial contraction;

wherein the conduit is generally T-shaped and the first conduit portion corresponds to one leg of the T having one free end while the second conduit portion corresponds to another leg of the T having two free ends, and wherein the two free ends of the other leg of the T define first and second outlets adapted to be placed in fluid communication with the lumen of the target vessel; and wherein at least one of the two free ends of the other leg of the T has a shaped tip for smooth introduction into the target vessel.

4. A device for placing a target vessel of a patient's vascular system in fluid communication with a heart chamber containing blood by forming a blood flow path between the target vessel and the heart chamber, the device comprising:

a conduit having first and second portions each of which has an axis, the axes of the first and second conduit portions being transverse to each other;

wherein the first conduit portion has a free end and is configured to be placed in fluid communication with a heart chamber containing blood, and the second conduit portion has two free ends that are sized and configured to be positioned at least partially within the lumen of a target vessel in the patient's vascular system;

wherein a diameter of the first conduit portion is greater than a diameter of the second conduit portion, and a channel defined by the first conduit portion is fluidly connected to a channel defined by the second conduit portion;

wherein the conduit is formed at least in part of a molded thermoset material having a predetermined amount of flexibility to permit the second portion of the conduit to be flexed for placement within the lumen of a target vessel; and wherein the first conduit portion has a length in the range of from about 30 mm to about 50 mm, while the second conduit portion has a length in the range of from about 3 mm to about 20 mm.

* * * * *